(12) United States Patent
Bekesi et al.

(10) Patent No.: US 6,294,695 B1
(45) Date of Patent: Sep. 25, 2001

(54) AMINOBENZOIC ACID DERIVATIVES HAVING ANTI-TUMORIGENIC ACTIVITY METHODS OF MAKING AND USING THE SAME

(75) Inventors: George J Bekesi, Edison, NJ (US); Jian-Dong Jiang; Imre Weisz, both of New York, NY (US); John Roboz, Riverdale; James F Holland, Scarsdale, both of NY (US)

(73) Assignee: Mount Sinai School of Medicine of the City University of New York

( * ) Notice: Subject to any disclaimer, the term of this patent is extended or adjusted under 35 U.S.C. 154(b) by 0 days.

(21) Appl. No.: 09/258,732

(22) Filed: Feb. 26, 1999

Related U.S. Application Data

(60) Provisional application No. 60/079,520, filed on Mar. 26, 1998.

(51) Int. Cl.$^7$ .................................................. C07C 237/28
(52) U.S. Cl. ........................ 564/161; 560/8; 562/553
(58) Field of Search ....................... 560/8; 564/161; 562/553

(56) References Cited

U.S. PATENT DOCUMENTS 4,093,739 * 6/1978 Martin .................................. 424/316

OTHER PUBLICATIONS

Alberts, et al., The Mechanics of Cell Division, *Molecular Biology of the Cell*, Garland: New York, 911–946 (1994).
Banerjee et al., Productive Non–lytic Hiv–1 Replication in a Newly Established Human Leukemic Cell Line, *Proc. Natl. Acad. Sci. U.S.A.*, 89, 9996 (1992).
Bekesi, G.J. et al., Translocation of Cytoplasmic Antigen Markers in a Biphenotypic Cell Line Derived from a Patient with Myelodysplastic Syndrome, *Molecular and Cellular Differentiation*, 3(2), 111 (1995).
Budesinsky, Z. et al., Synthetic Antidiabetics I. Derivatives of Urea, Thiourea and Guanidine, *Czechoslovak Pharmaceutics*, 8, pages 129ff (1959) (including translation).
Kerr, J.F.R. et al., Apoptosis: its significance in Cancer and Cancer Therapy, *Cancer* 73(8), 2013 (1994).
Milas, L. et al., Kinetics of Mitotic Arrest and Apoptosis in Murine Mammary and Ovarian Tumor Treated with Taxol, *Cancer Chemother. Pharmacol.*, 35, 297 (1995).
Roboz, J. et al., Selective Tumor Apoptosis by Mf13, L–prolyl–l–m–[Bis(chloroethyl)amino]–phenylkala-nyl–l–norvaline Ethyl Ester, a Sacolysin Cotnaining Tripeptide, *Cancer Research*, 57, 495 (1997).
Shi, Y. et al., Role for C–myc in Apoptotic Cell Death in T–cell Hybridoma, *Science* 257, 212 (1992).
Takano, Y. et al., Apoptosis Induced by Microtubule Disrupting Drugs in Cultured Human Lymphoma Cells. Inhibitory Effects of Phorbol Ester and Zinc Sulphate, *Pathol. Res. Pract.*, 189, 187 (1993).
Weisz, I. et al., Acidic Coupling and Aminolytic Tfa Cleavage Approaches in a New Synthesis of L–m–sarcolysm Containing Antitumor Tripeptide Ester, *Tetrahedron Letters*, 37, 563 (1996).
Weisz, I. et al., Acylation of Alcohols, Amines and Amine Salts with Acid Chlorides in the Presence of Amides, *Arch. Pharm. (Weinheim)* 318, 766–768 (1985) (including translation).
Weisz, I. et al., "N–Substituted Carbamate Esters and Carboxamides," *Chem. Abstract* 88, 152278 (1978).
Wyllie, A.H., et al., Cell Death: the Significance of Apoptosis, *Inter. Rev. of Cytol.*, 68, 251 (1980).

* cited by examiner

*Primary Examiner*—Christopher S. F. Low
*Assistant Examiner*—David Lukton
(74) *Attorney, Agent, or Firm*—Baker Botts L.L.P.

(57) ABSTRACT

Haloacetoamido, benzoic acid derivatives having anti-tumorigenic activity are inclosed. Examples of the haloacetoamido, benzoic acid derivatives include 3-chloroacetoamido, benzoylurca, 3-bromoacctoamido, benzoylurea, 3-todoacetoamido, benzoylurca, ethyl-3-chloroacetoamido, benzoate, ethyl-3-bromoacetoamido, benzoate and ethyl-3-iodoacetoamido, benzoate. Intermediates for synthesizing the derivatives, along with method of making and using the derivatives, are also provided.

10 Claims, 10 Drawing Sheets

AMINOBENZOIC ACID DERIVATIVES HAVING ANTI-TUMORIGENIC ACTIVITY METHODS OF MAKING AND USING THE SAME

This application claims priority under 35 U.S.C. §119(e) from Provisional Application No. 60/079,520 filed Mar. 26, 1998.

FIELD OF THE INVENTION

The present invention relates to aminobenzoic acid derivatives that exhibit anti-tumorigenic activity, and more particularly to haloacetylated, aminobenzoic acid derivatives that exhibit anti-tumorigenic activity.

BACKGROUND OF THE INVENTION

Cancer is a disease that afflicts many in the general population. As a result, a variety of therapies have been developed for treating these malignancies, such as radiation, chemotherapeutics, antisense oligonucleotides, monoclonal antibodies and vaccines. However, even with these therapeutic options, cancer still remains a serious life threatening disease.

In addition to radiation and surgery, chemotherapy is a standard treatment option for those diagnosed with a malignancy. Numerous compounds have been tested and approved for use. However, most chemotherapeutics while being toxic to malignant cells are unfortunately toxic to normal cells. As a result, the side effects of chemotherapeutics are often severe. Recipients of chemotherapeutics often develop complications such as immune suppression which often lead to a variety of opportunistic infections. In many circumstances, patients do not succumb to the cancer, but to the side effects of the chemotherapy.

The development of promising chemotherapeutics is also hampered by the unavailability of large quantities of the potential agent for clinical trials. The vast majority of chemotherapeutics have complex multi-cyclic structures that renders synthesis difficult at best. Thus, natural sources of the potential agent, which are often limited, can become a limiting factor in widespread assessment of anti-neoplastic efficacy of the potential agent.

Accordingly, there is a continuing need in the art for new chemotherapeutics for the treatment of cancer, and especially chemotherapeutics that can be readily synthesized by conventional organic techniques. There is also a need in the art for chemotherapeutics that exhibit preferential toxicity to malignant cells to minimize the unwanted side effects commonly associated with chemotherapeutic agents.

It is, therefore, an object of the present invention to provide new agents for inhibiting tumor cell growth, which can be readily synthesized by conventional organic techniques. It is also an object of the present invention to provide agents that exhibit preferential toxicity to malignant cells.

SUMMARY OF THE INVENTION

The present invention provides a class of compounds useful for the inhibition of malignant cell growth (e.g., tumors). In one embodiment, the present invention provides m-haloacetoamido, benzoic acid derivatives having the formula:

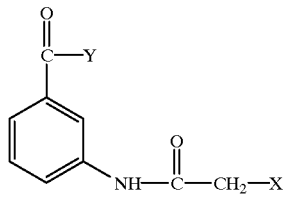

(I)

wherein X is a halogen selected from the group consisting of chlorine, bromine and iodine, and independently Y is a substituent selected from the group consisting of urea, ethoxide, —NH—CO—NH—R, wherein R is hydrogen, an alkyl or an aryl, and —N—$R_1$, wherein $R_1$ is an alkyl, a heterocyclic or an amino acid ester, or an acid addition salt thereof. Examples of the m-haloacetoamido, benzoic acid derivatives are 3-chloroacetoamido, benzoylurea, 3-bromoacetoamido, benzoylurea, 3-iodoacetoamido, benzoylurea, ethyl-3-chloroacetoamido, benzoate, ethyl-3-bromoacetoamido, benzoate and ethyl-3-iodoacetoamido, benzoate.

In another embodiment, the present invention provides p-haloacctoamido, benzoic acid derivatives having the formula:

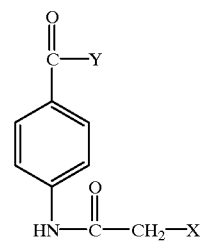

(II)

wherein X is a halogen selected from the group consisting of chlorine, bromine and iodine, and independently Y is a substituent selected from the group consisting of urea, ethoxide, —NH—CO—NH—R, wherein R is hydrogen, an alkyl or an aryl, and —N—$R_1$, wherein $R_1$ is an alkyl, a heterocyclic or an amino acid ester, or an acid addition salt thereof Examples of the p-haloacetoamido, benzoic acid derivatives are 4-chloroacetoamido, benzoylurea, 4-bromoacetoamido, benzoylurea, 4-iodoacetoamido, benzoylurea, ethyl-4-chloroacetoamido, benzoate, ethyl-4-bromoacetoamido, benzoate and ethyl-4-iodoacetoamido, benzoate.

The present invention also provides intermediate compounds for synthesizing the meta-and para-haloacetoamido, benzoic acid derivatives. In one embodiment, the present invention provides an aminobenzoic acid derivative, having the formula:

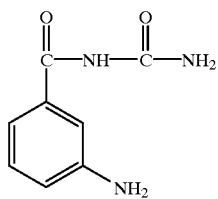

(III)

In another embodiment, the present invention provides as aminobenzoic acid derivative, having the formula:

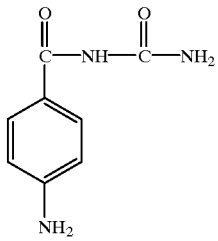

(IV)

A method of inhibiting the growth of malignant cells is provided by administering to the cells, an effective amount of the haloacetoamido, benzoic acid derivatives of formula (I) or an acid addition salt thereof. A method of inhibiting the growth of malignant cells is also provided by administering to the cells an effective amount of a haloacetoamido, benzoic acid derivative of formula (II) or an acid addition salt thereof. The present invention also provides a method of inhibiting mitosis in malignant cells by treating the cells with an effective amount of a haloacetoamido, benzoylurea derivatives of formula (I) or an acid addition salt thereof.

The present invention also provides methods of synthesizing the compounds of formula (I), (II), (III) and (IV). In addition to formulations containing effective amounts of the haloacetoamido, benzoic acid derivatives of formula (I), (II), or their acid addition salts, in a physiologically acceptable carrier, are provided.

Advantageously, the compounds of the present invention are effective in inhibiting malignant cell growth, while exhibiting significantly reduced cytotoxicity to normal cells. The compounds of the present invention also provide the advantage of a simple cyclic structure which can be readily synthesized by those skilled in the art. These and other advantages of the present invention are further described below.

BRIEF DESCRIPTION OF THE DRAWINGS

FIG. 3A =untreated cells; FIG. 3B=CEM cells treated with 8 at 0.025 $\mu$g/ml for 24 h; FIG. 3C=cells treated with 9 at 0.005 $\mu$g/ml for 24 h, showing mitotic arrest–FIG. 3D=cells in apoptotic stage after 48 h treatment with 8 at 0.025 $\mu$g/ml. FIGS. 3A, B, and C were taken with Giemsa X400, while FIG. 3D was taken with Giemsa, oil immersion.

(FIG. 8A) free tubulins in reaction buffer were incubated with GTP and Mg$^{2+}$ at 37° C. for the assembly process in the absence or presence of 3-BAABU (3.3 $\mu$M) or paclitaxel (23 $\mu$M) or vinblastine (22 $\mu$M)

DETAILED DESCRIPTION OF THE INVENTION

Figure 1:
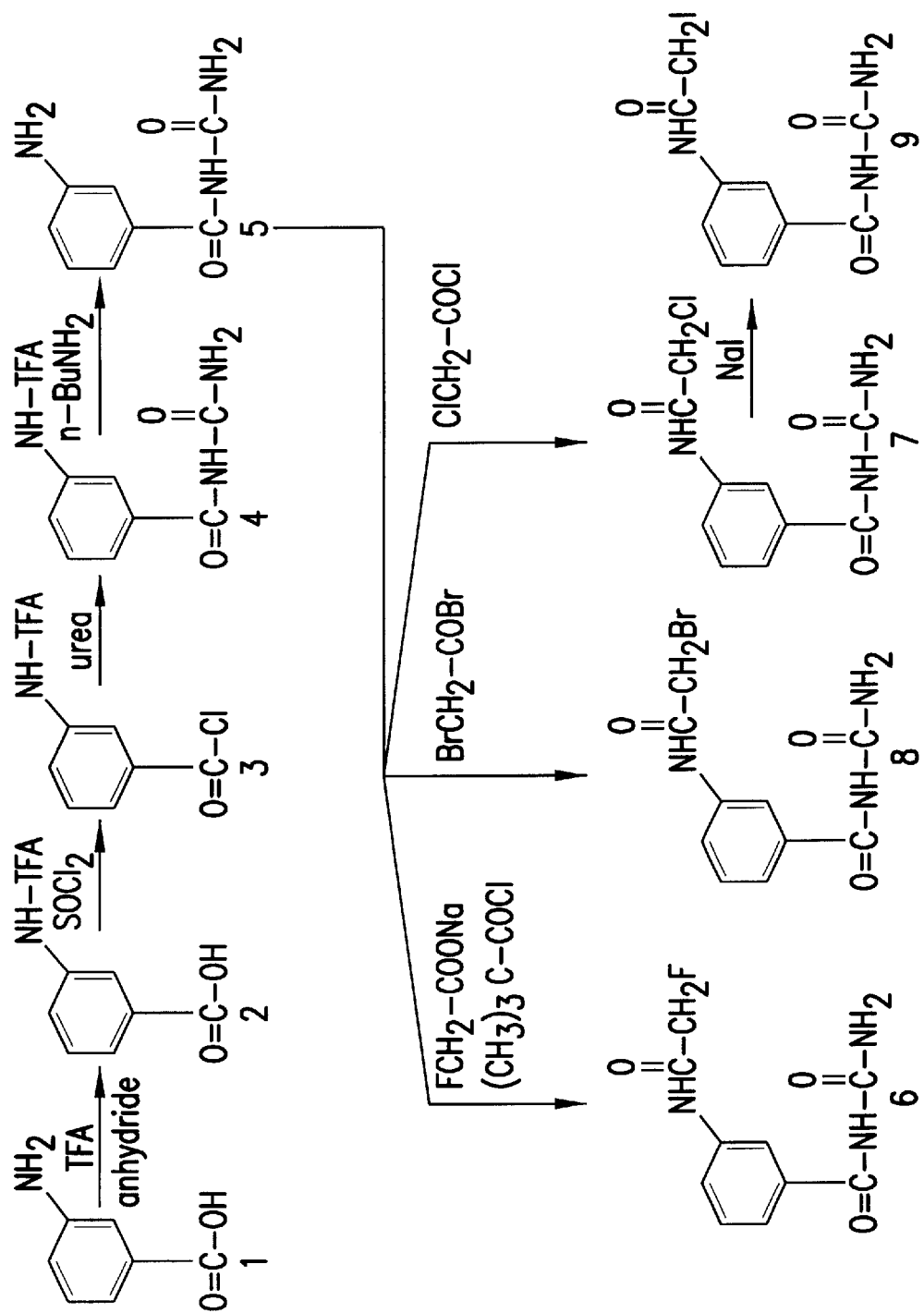
FIG. 1 is a reaction scheme illustrating the synthesis of the 3-haloacetoamido, benzoylurea derivatives, of the present invention.
Figure 2A:
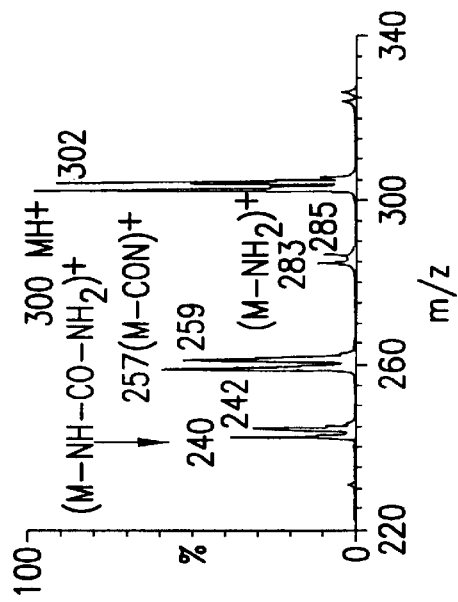
FIGS. 2A–2D are electrospray mass spectra of: (I) compound 8, 3-bromo-acetoamido, benzoylurea (see FIG. 1) at a cone voltage of 25 Volts (V) (FIG. 2A) and at 48 V (FIG. 2B); and (II) compound 9, (3-iodoacetoamido, benzoylurea (see FIG. 1) at a cone voltage of 25 V (FIG. 2C) and 48 V (FIG. 2D).
Figure 2B:
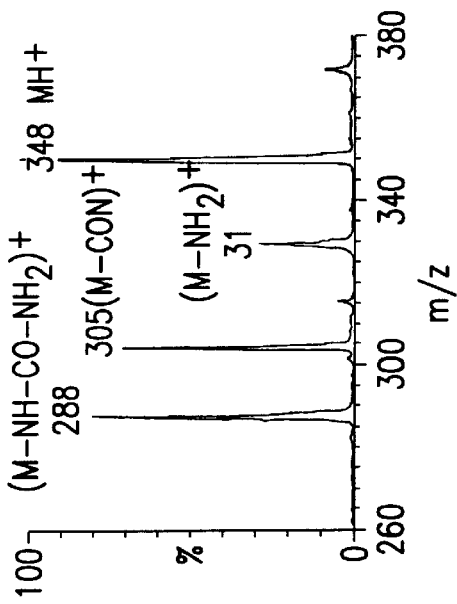
Figure 2C:
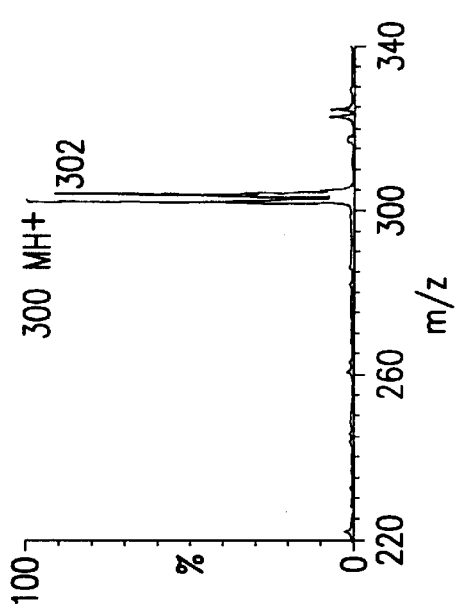
Figure 2D:
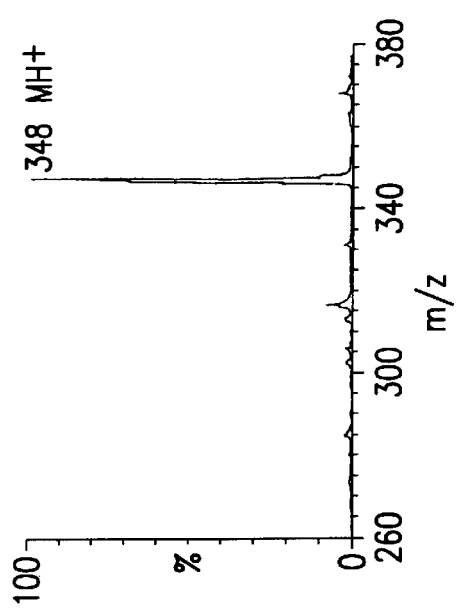
Figure 3A:
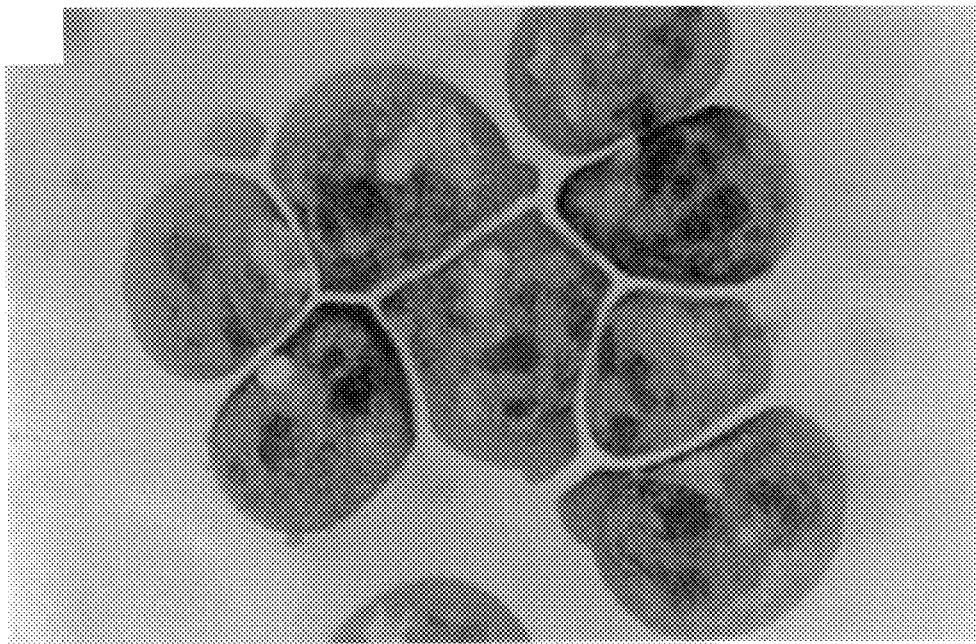
FIGS. 3A–D are photographs illustrating the morphological appearance of cells of the CEM leukemia cell line in mitotic arrest induced by compounds 8 and 9.
Figure 3B:
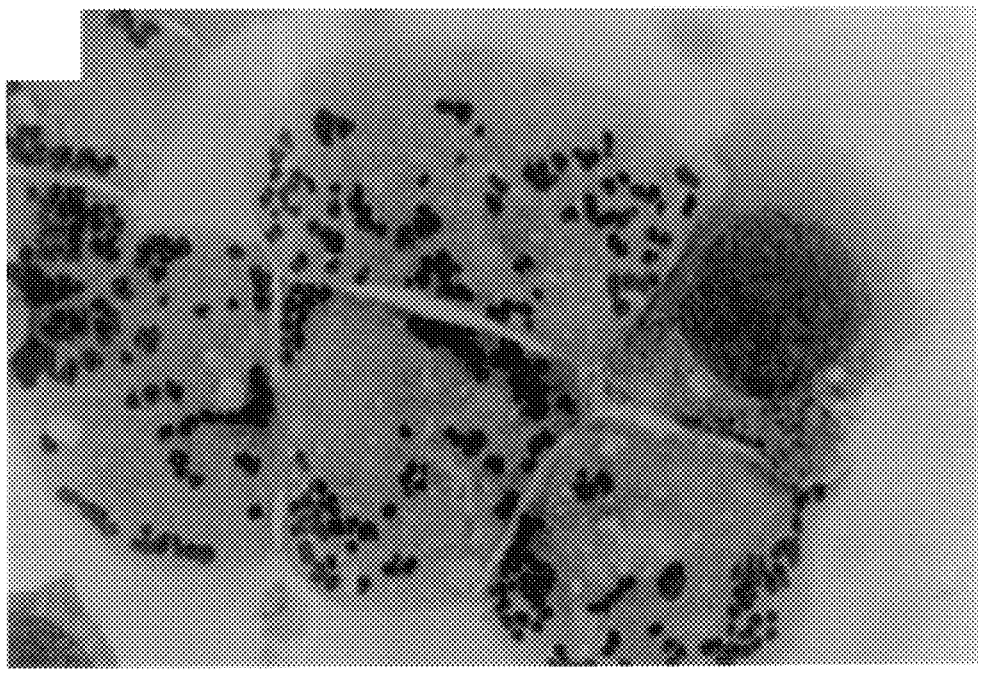
Figure 3C:
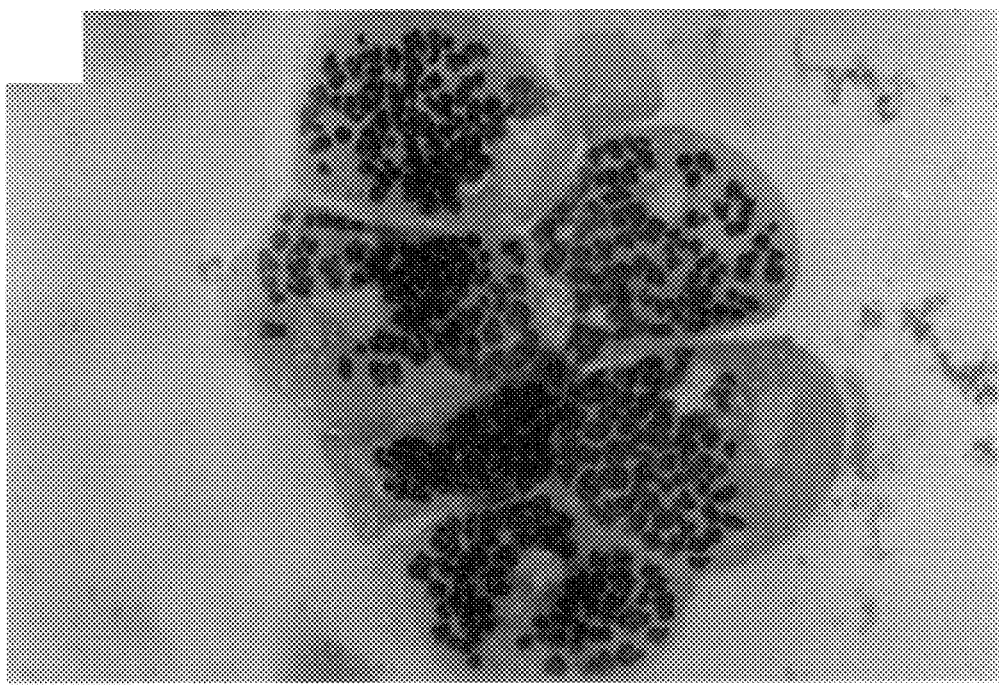
Figure 3D:

The present invention provides a new class of compounds useful for the inhibition of malignant cell growth (e.g., tumors). The compounds have preferential effectiveness in regard to malignant cells in that, at equivalent doses, the compounds of the present invention are preferentially cytotoxic to malignant cells, but not to normal cells.

In a first embodiment, the present invention provides meta-haloacetoamido, benzoic acid derivatives having the formula:

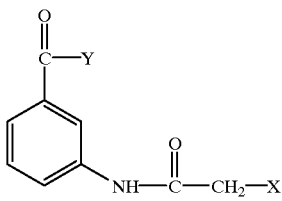

(I)

wherein X is a halogen selected from the group consisting of chlorine, bromine and iodine, and independently Y is a substituent selected from the group consisting of urea, ethoxide, —NH—CO—NH—R, in which R is hydrogen, an alkyl or an aryl, and —N—R$_1$, in which R$_1$ is an alkyl, a heterocyclic (e.g., 2-aminothiazole) or an amino acid ester (e.g., proline methyl ester (NC$_6$O$_2$H$_{10}$). The term "independently" means that the selection of substituents X and Y are independent from each other.

Preferably, the X substituent is bromine or iodine, with iodine being more preferred since it has been found that iodine provides the compound with greater anti-tubule activity and, therefore, greater apoptotic activity. The Y substituent is also preferably a urea mioety if anti-tubule activity is desired. However, the Y substituent can also be an ethoxy group or one of the other above-described groups thereby eliminating anti-tubule activity while retaining apoptotic activity.

Examples of the haloacetoamido, benzoylurea derivatives having anti-tubule activity are 3-chloroacetoamido, benzoylurea, 3-bromoacetoamido, benzoylurea, and 3-iodoacetoamido, benzoylurea. Examples of ethyl-haloacetoamido, benzoate derivatives having apoptotic activity are ethyl-3-chloroacetoamido, benzoate, ethyl-3-bromoacetoamido, benzoate and ethyl-3-iodoacctoamido, benzoate.

In a second embodiment of the present invention, an additional class of para-haloacetoamido, benzoic acid derivatives is provided. These compounds, unlike the above describe compounds, preferentially induce necrosis in malignant cells. These necrosis-inducing compounds have the formula:

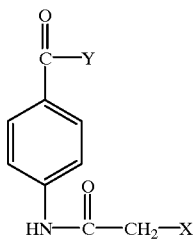

(II)

wherein X is a halogen selected from the group consisting of chlorine, bromine and iodine, and independently Y is a substituent selected from the group consisting of urea, ethoxide, —NH—CO—NH—R, in which R is hydrogen, an alkyl or an aryl, and —N—R$_1$, in which R$_1$ is an alkyl, a heterocyclic (e.g., z-aminothiazole) or an amino acid ester (e.g., proline methyl ester (NC$_6$O$_2$H$_{10}$). Unlike the meta-substituted isomers described above, the para-substituted isomers of the haloacetoamido, benzoic acid derivatives do not induce apoptosis in malignant cells, but induce an alternative form of cell death, necrosis. Thus, the present invention provides two alternative classes of cytotoxic compounds for inhibiting malignant cell growth.

Examples of the para-substituted haloacetoamido, benzoylurea derivatives having necrotic activity are 4-chloroacetoamido, benzoylurea, 4-bromoacetoamido, benzoylurea, and 4-iodoacctoamido, benzoylurea. Examples of ethyl-haloacetoamido, benzoate derivatives are ethyl-4-chloro ethylbenzoate, ethyl-4-bromoacetoamido, benzoate and ethyl-4-iodoacctoamido, benzoate.

The present invention also includes intermediate compounds (meta- and para-position isomers of compound 5 shown in FIG. 1) particularly suitable for synthesizing the haloacetoamido, benzoylurea derivatives of above described classes of anti-tumorigenic compounds. Both intermediate compounds are utilized in the reaction scheme shown in FIG. 1 as compound 5. The first intermediate compound is a meta-substituted, aminobenzoic acid derivative (3-aminobenzoylurea) having the formula:

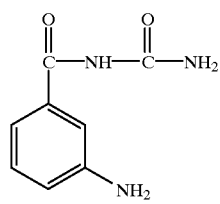

(III)

The second intermediate compound is apara-substituted, aminobenzoic acid derivative (4-aminobenzoylurea) having the formula:

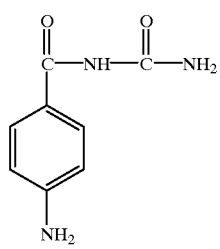

(IV)

The anti-tumorigenic compounds of the present invention may also be provided as an acid addition salt to increase their solubility in an aqueous solution. Preferably, the acid addition salt is a physiologically acceptable acid addition salt in that the salt moiety is tolerable to a mammal at conventional dosages. In accordance with the present invention, the anti-tumorigenic compounds may be converted to an acid addition salt following conventional techniques known to one skilled in the art.

The compounds of the present invention are administered to a malignant cell growth in an effective amount. An effective amount is any amount of the compound that inhibits the growth or proliferation of the malignant cells and preferably reduces the size of a tumor. Preferably the compounds are administered to a mammal with a malignant cell growth, who is therefore in need of such treatment. Examples of mammals to be administered the compounds of the present invention include, but are not limited to, humans, equines, canines, felines, murines and bovines. A mammal is in need of treatment if it has been diagnosed with a malignancy following conventional diagnostic protocols. Examples of malignancies that may be amenable to inhibition of growth by the above described compounds of the present invention, include, but are not limited to, prostate cancer, colon cancer, breast cancer, kidney cancer, leukemia, lymphoma, melanoma, and myclodysplastic syndrome.

As will be apparent to one of ordinary skill in the art, the actual dosage that will provide an effective amount to the mammal is dependent on a variety of factors. Examples of factors to be considered include, but are not limited to, age, weight, sex, the stage of the malignancy, the existence of immune suppression and other medical complications. For example, the anti-tumorigenic compounds of the invention may be administered at a dosage of at least 0.1 mg/kg, with at least 1 mg/kg being preferred, and at least 10 mg/kg being more preferred, with no more than 100 mg/kg being preferred, with no more than 50 mg/kg being more preferred, and no more than 30 mg/kg being even more preferred.

The anti-tumorigenic compounds of the present invention are administered to (or contacted with) a malignant cell growth by any technique know in the art. The compounds may be administered to the mammal via known drug delivery routes which include, but are not limited to, oral, topical, intravenous, intranasal, and pulmonary delivery. Preferably, the anti-tumorigenic compounds of the present invention, as with other chemotherapeutics, are administered to the mammal by intravenous injection. Alternatively, the compounds can be injected directly into the tumor.

The present invention also includes formulations containing effective amounts of the anti-tumorigenic compounds, or acid addition salts thereof, in a physiologically acceptable carrier. A physiologically acceptable carrier is any carrier that can be tolerated by a mammal at conventional dosages. The choice of the carrier is dependent on the dosage form, e.g., buffered saline for injection, which can be easily determined by one skilled in the art.

The compounds of the present invention can be synthesized by one skilled in the art following conventional organic synthesis techniques. However, a preferred method of synthesizing the haloacetoamido, benzoylurea derivatives of the present invention is shown in the reaction scheme in FIG. 1. As will be apparent to one skilled in the art, the only distinction between synthesizing the meta-haloacetoamido, benzoylurea and the para-haloacetoamido, benzoylurea derivatives is the starting compound (i.e., meta-aminobenzoic acid versus para-aminobenzoic acid). The ethyl-haloacetoamido, benzoate derivatives of the present invention are synthesized in a one step mechanism by reacting either ethyl-3-aminobenzoate or ethyl-4-aminobenzoate (i.e., benzocaine) with a suitable halogenating agent, such as iodoacetyl iodide, bromoacetyl bromide or chloroacetyl chloride, or replacement of chlorine with iodine using sodium iodide (NaI).

The following non-limiting examples illustrate the synthesis of the compounds of the present invention and their use in inhibiting malignant cell growth.

EXAMPLES

Example I

A. Materials and Methods
1. Synthesis of the Halogenated Benzoylurca and Ethyl Benzoate Derivatives All commercial chemicals were purchased from Aldrich Chemical Co., Milwaukee, Wis. The techniques for the syntheses of the 3-position (m, meta) compounds are described with reference to the reaction scheme shown in FIG. 1, which identify Compounds 1–9; the bromine and iodine compounds in the 4-position (p, para) were synthesized in an identical manner from p-4-aminobenzoic acid (Compound 1).

3-Trifluoroacetyl-aminobenzoic acid (Compound 2). 13.7 g (0.1 mole) 3-aminobenzoic acid (compound 1), 15.53 ml (0.11 mole) trifluoroacetic anhydride were reacted in 140 ml EtAc at 65° C. for 1 h. The solid product was filtered and washed with EtAc. Yield: 20.0 g (86%), m.p. 285° C. For the 4-position isomer, yield 21.0 g (87%), m.p. 285° C.

3-Trifluoroacetyl-aminobenzoyl chloride (Compound 3). 4.66 g (0.02 mole) of Compound 2, 50 ml EtAc and 15 ml $SOCl_2$ were refluxed until the reaction mixture became a clear, yellow solution (1 h). After removing the solvent and excess reagent, the residue was crystalized from n-hexane. Yield: 4.5 g (85%), m.p. 95–98° C. For the 4-position isomer, yield 4.2 g (81%), m.p. 112–114° C.

3-Trifluoroacetyl-aminobenzoylurea (Compound 4). A stirred mixture of 5.2 g (0.02 mole) of Compound 3 and 6.00 g (0.1 mole) of urea in 50 ml toluene was slowly heated (approx. 20 min) until voluminous precipitation stopped the stirrer at 100° C. (below the boiling point of toluene). The mixture was cooled to 50° C. and the solvent was removed in vacuum. 100 ml water was added to the residue to remove excess urea. After filtration, the white crystals were washed with water and ethanol. Yield: 5.0 g (91%), m.p. 253–256° C. For the 4-position isomer, yield 5.4 g (99%), m.p. >300° C.

3-Aminobenzoylurea (Compound 5). 2.75 g (0.01 mole) of Compound 4, 20 ml methanol, and 15 ml n-butylamine were refluxed for 80 min. The solvent and excess butylamnine were removed in vacuum, 20 ml diethyl ether was added to the residue and the solid product of the reaction was filtered and washed with methanol. Diethyl ether was used because Compound 5 is insoluble in ether while TFA-n-butylamine, the other product of the aminolysis, is very soluble in ether. Yield: 1.5 g (82%), m.p. >300° C. of both the 3- and 4-position compounds.

3-Fluoroacetoamido, benzoylurea (Compound 6). 8.0 g (0.08 mole) fluoroacetic acid-Na and 7.8 g (0.065 mole) trimethylacetyl chloride was reacted in 50 ml N,N-dimethylacetamide at 65° C. for 1 h. After cooling to 20° C., 3.94 g (0.02 mole) of Compound 5, dissolved in 12 ml N,N-dimethylacetamide, was added. After keeping the mixture at 20° C. for 2.5 h, 300 ml ice water and 20 ml EtAc were added and the mixture stirred for 10 min. The precipitate was filtered and washed with water and ethanol. Yield: 1.3 g (25.9%), m.p. 241–245° C.

3-Chloroacetoamido, benzoylurea (Compound 7). 1.79 g (0.01 mole) of Compound 5 was reacted with 2.0 ml chloro-acetyl chloride in 15 ml N,N-dimethylacetamide at room temperature for 2 hr. After adding 200 ml ice water, the solid precipitate was filtered, washed with water, and boiled in 10 ml ethanol for 20 min. filtered and washed with ethanol again. Yield: 1.8 g (70.0%), m.p. 265° C.

3-Bromoacctoamido, benzoylurea (Compound 8) was prepared with bromoacetyl bromide in the same manner except using methanol instead of ethanol for final purification. Yield: 2.05 g (68.0%), m.p. 238–242° C. For the 4-position isomer, yield 65%, m.p. 250–255° C.

3-Iodoacetoamido, benzoylurea (Compound 9). 2.55 g (0.01 mole) of Compound 7 and 6 g NaI were reacted in 10 ml N,N-dimethylacetamide at room temperature for 80 min. After adding 200 ml ice water, the solid precipitate was filtered, washed with water, boiled in 25 ml ethanol for 1 h, filtered and washed with ethanol several times. Yield: 3.07 g (88.0%), m.p. 270–274° C. For the 4-position isomer, yield 86%, m.p. 250–253° C.

Ethyl-3-chloroacetoamido, benzoate (Compound 10, not shown in FIG. 1) was synthesized from ethyl 3-aminobenzoate (3.3 g, 0.02 mole) dissolved in N,N-dimethylacetamide (20 ml) by reacting with chloroacetyl chloride (3.4 g, 0.03 mole) at 20° C. for 2 h. The solid precipitate that formed after the addition of ice water was filtered and recrystallized from alcohol. Yield 3.4 g (72%), m.p. 80–82° C.

Ethyl-3-bromoacetoamido, benzoate (Compound 11, not shown in FIG. 1) was synthesized the same way, using bromoacetyl bromide. Yield 3.0 (51.8%), m.p. 83–85° C.

2. Malignant Cells for Toxicology Studies

CEM cells, a human T-cell lymphoblastoid leukemia cell line (American Type Culture Collection, Rockville, Md.), were cultured in suspension (Iscove's Dulbecco's Medium) supplemented with 10% heat inactivated fetal bovine serum (FBS), penicillin (250 $\mu$/ml) and streptomycin (250 $\mu$l/ml). Cells were incubated at 37° C. in 5% $CO_2$ and only those cells in exponential growth were used.

3. Determination of $ID_{50}$ and $ID_{90}$ by Trypan Blue Staining

CEM cells were seeded into 96-well microplates (Falcon, Oxnard, Calif.) at $10^5$ cell per well, then treated with 0–10 $\mu$g/ml of the candidate compounds for 48 h at 37° C. yielding a total volume of 250 $\mu$/well. Cell viability was assessed by trypan blue staining. $ID_{50}$ and $ID_{90}$ were defined as the concentration killing 50% or 90% of the cells in comparison with untreated controls, and calculated by non-linear regression analysis.

4. Morphology by Microscopy

Slides for examination of mitosis were prepared on a cytospin centrifuge (Shandon Southern Products Ltd, England) at 700 g for 5 min. Slides were air dried, fixed in methanol and stained with Giemsa (Harleco, N.J.) at room temperature for 15 min. Cells in mitotic arrest were recognized by the disappearance of nuclear membrane and by the appearance of chromosomal scattering throughout the cytoplasm (reference 1). The % of mitotic cells were counted after 24 h incubation using optical microscopy. Apoptotic cells were identified using common criteria, i.e., shrinkage in cell size, chromatin condensation and fragmentation of the nucleus into discrete masses (reference 2).

5. Cell Cycle Analysis by Flow Cytometry

Cell cycle was measured by determining DNA content as described by the manufacturer of the Cycle Test kit (Becton Dickinson, San Jose, Calif.). At least $10^4$ CEM cells were analyzed. Properties of the light-scattering (forward and sideward) and DNA luminescence of individual cells were measured with a FAC Scan flow cytometer using Cellfit software for gating analysis (Becton Dickinson, San Jose, Calif.).

6. DNA Fragmentation by Electrophoresis

DNA fragmentation was determined by a method reported previously (reference 3). Briefly, cells were treated in 1 ml lysis buffer (0.01M Tris. HCL pH 8.0, 0.01M NaCl, 0.01M EDTA pH 8.0 and 5% sodium dodecyl sulfate) containing 1 $\mu$g/ml protease K for 1 h at 50° C. The resulting products were extracted with phenol and chloroform:isoamylalcohol (24:1, v/v), and precipitated with ethanol followed by centrifugation at 7800 g (SorvallRC-5B Du Pont, Newtown, Conn.). The ethanol was removed and the dry pellets of nucleic acid were resuspended in 10 mM Tris-HCL/1 mM EDTA solution. When DNA content was determined spectrophotometrically all samples had $A_{260}/A_{280}$ ratio $\geq 2$. The DNA samples were then treated with RNase (Sigma, St. Louis, Mo.) at a final concentration of 0.1 $\mu$g/$\mu$l for 20 min at 37° C. before gel loading. Approximately 4 $\mu$g size DNA aliquots were loaded onto horizontal agarose gel (1.5%) prepared with 1% ethidium bromide. Electrophoresis was performed at 75 volts for 2 h and the DNA patterns were visualized with UV light.

7. Inhibition Assay of Microtubule Assembly and Disassembly by Spectrophotometry Purified tubulin was purchased from Sigma (St. Louis, Mo.). The effects of compounds 6, 7, 8, 9, paclitaxel and vinblastine on the microtubule assembly-disassembly process were determined using conditions recommended by the vendor. For assembly inhibition, 100 $\mu$l tubulin solution (500–600 $\mu$g protein/ml) was mixed gently with 400 $\mu$l reaction buffer containing 0.1 M MES (2-[N-moipholino] ethane sulfonic acid), 1 mM EGTA (ethylene glyco-bis[β-aminoethyl ester]-N,N,N',N'-tetraacetic acid), 0.5 mM $MgCl_2$, 0.1 mM EDTA and 2.5 M glycerol at 37° C. Compounds 6, 7, 8, and 9 were next added to each sample at final concentrations of 10, 10, 1 and 1 $\mu$g/ml, respectively. After adding GTP to each sample to a final concentration of 1 mM, the microtubule assembly process was monitored by measuring the change of absorbance (OD) at 350 nm on a spectrophotometer (Ultrospec III, Pharmacia LKB, Uppsala, Sweden). A completed assembly process was observed within 40 min at room temperature. For disassembly inhibition, compounds 6, 7, 8, and 9 were added, at the above concentrations, to covets with repolymerized microtubules as described above, and incubated in melting ice. Changes of absorbance (OD) were monitored at 350 nm for 30 min until the OD values in the controls returned to the starting level, i.e., when the assembly-disassembly cycle was completed.

B. Results and Discussion

1. Synthesis

All four target compounds, 6, 7, 8, 9 were prepared from a key intermediate, 3-aminobenzoylurea, compound 5 (See reaction scheme in FIG. 1). Starting with commercially available 3-aminobenzoic acid, the TFA-derivative, compound 2, was prepared by conventional trifluoroacetylation. The N-protected amino acid was next transformed to its acid chloride, compound 3, with the aid of $SOCl_2$. Urea was introduced by using compound 3 as an acylating reagent to yield compound 4 (reference 4). Removal of the TFA group was accomplished by a novel aminolytic deprotection technique described by us earlier (reference 5). This led to compound 5, the key intermediate. The four haloacetyl compounds were derived from compound 5 by operationally convenient routes. Because fluoroacetyl chloride is not readily available, the fluorine compound, compound 6, was prepared using Na-fluoroacetate and trimethylacetyl chloride in N,N-dimethylacetamide. The chlorine and bromine compounds, compounds 7 and 8, were prepared in a similar manner with chloroacetyl chloride and bromoacetyl bromide, respectively. N,N-dimethylacetamide was the solvent not only because it is capable of dissolving these compounds, but also because it binds the liberated halogenic acids while keeping the system acidic (reference 6). The acidic medium, which results immediately upon adding the acid halide reagent, allows the acylation of the aromatic amino group (reference 7). The acid binding property of the solvent obviated the need for the addition of any base thus effectively preventing the acylation of the urea-$NH_2$ group. The iodine compound, compound 9, was prepared from the chlorine compound, compound 7, by an exchange reaction using NaI. In addition to the 3-isomer (meta), the bromoacetyl and iodoacetyl derivatives in the 4-isomer (para) position were also prepared as described for compounds 8 and 9.

2. ¹H NMR Data

Spectra were recorded with a Bruker AC 200 MHZ spectrometer in $CD_3OD$ or $DMSO-D_6$ solution. Compound 8: δ 6–8.8275 (ddd, 1 H, 2-aromatic H), δ 7.9217 (ddd, 1 H, 6-aromatic H), δ :7.6556 (ddd 1 H, 4-aromatic H), δ 7.4188 (ddd, 1 H, 5-aromatic H), δ 4.0248 (s 2H $CH_2Br$), δ 10.3787, 9.7922, 8.9437 (s, s, br, 4 H, amido NH, urea NH, amino $NH_2$) ppm. Para isomer of compound 8: δ 7.9662 (dd, 2 H, 3, 3'-aromatic H), δ 7.8246 (dd, 2 H, 2,2'-aromatic H), δ 6 4.0433 (s 2H $CH_2Br$), δ 10,3013, 9.9533, 6.1276 (s, s, br, 4 H, amido NH, urea NH, amino $NH_2$) ppm. Compound 9: δ 7.7051 (ddd, 1 H, 2-aromatic H), δ 7.6429 (ddd, 1 H, 5-aromatic H), δ 3.8842 (s 2 H $CH^2I$), δ 4.7(br, 4 H, urea NH, amino $NH_2$ exchanging with residual $CH_3OH$) ppm. Results were similar for compounds 6 and 7.

3. Identification by Mass Spectrometry.

The identity of every intermediate product was confirmed by electrospray ionization (E.I.) mass spectrometry (Model Quattro triple quadruple instrument, Bisons, Altrincham, GB). The conventional E.I. spectrum of the bromine compound 8 (mol. wt. 300 Da) revealed abundant protonated molecular ions, the expected bromine isotope ratios and not much else (FIG. 2, Panel A). When the cone voltage was increased, several structurally important fragment ions appeared (FIG. 2, Panel B). The results were similar for the iodine compound 9 (mol. wt. 347 Da., FIG. 2, Panels C and D). The relative intensities of the fragment ions were structure dependent, permitting, together with differences in chromatographic behavior, the differentiation of the highly bioactive meta and the biologically inactive para isomers of the bromine and iodine compounds despite their identical molecular weights. The mass spectra of the fluorine compound (mol. wt. 239 Da.) and the chlorine compound (mol. wt. 256 Da.) were similar to those described above.

4. Determination of $ID_{90}$

The cytotoxicity of compounds 6, 7, 8, and 9 against human leukemic cells (CEM), depended on the nature of the halogen (see Table 1). The fluorine compound 6 expressed no cytotoxicity even at a concentration as high as 10 μM. At the other extreme, the iodine compound 9 was 160-fold more toxic than the chlorine compound 7 and 5-fold more toxic than the bromine compound 8. Thus, the compounds were ranked according to their cytotoxicity as I>Br>Cl>F.

With respect to the position of the halogens, the 3-position (meta) yielded significantly higher cytotoxicity than the 4-position (para) for both the bromine and iodine compounds (see Table 1). It is clear that the 3-position of the halogen is preferred for cytotoxicity. Cytotoxicity was reduced significantly when the compounds did not contain the urea moiety (compounds 10 and 11, see Table 1), thus the presence of the urea is preferred for optimal cytotoxicity of compounds 8 and 9.

5. Mitotic Arrest

The mitotic arrest (blocking) effect of the compounds are best illustrated by comparing the morphological appearance of untreated CEM leukemic cells (FIG. 3, Panel A) with those after treatment for 24 h with 0.025 μg/ml of compound 8 (FIG. 3, Panel B) and 0.005 μg/ml of the more cytotoxic compound 9 (FIG. 3, Panel C) which reveal the main features of mitotic arrest, i.e., the disappearance of nuclear membrane and disorientation and loose dispersion of metaphase chromosomes in the cytoplasm. The fluorine compound 6 failed to induce mitotic arrest, and the effect of the chlorine compound 7 was minor.

Figure 4:
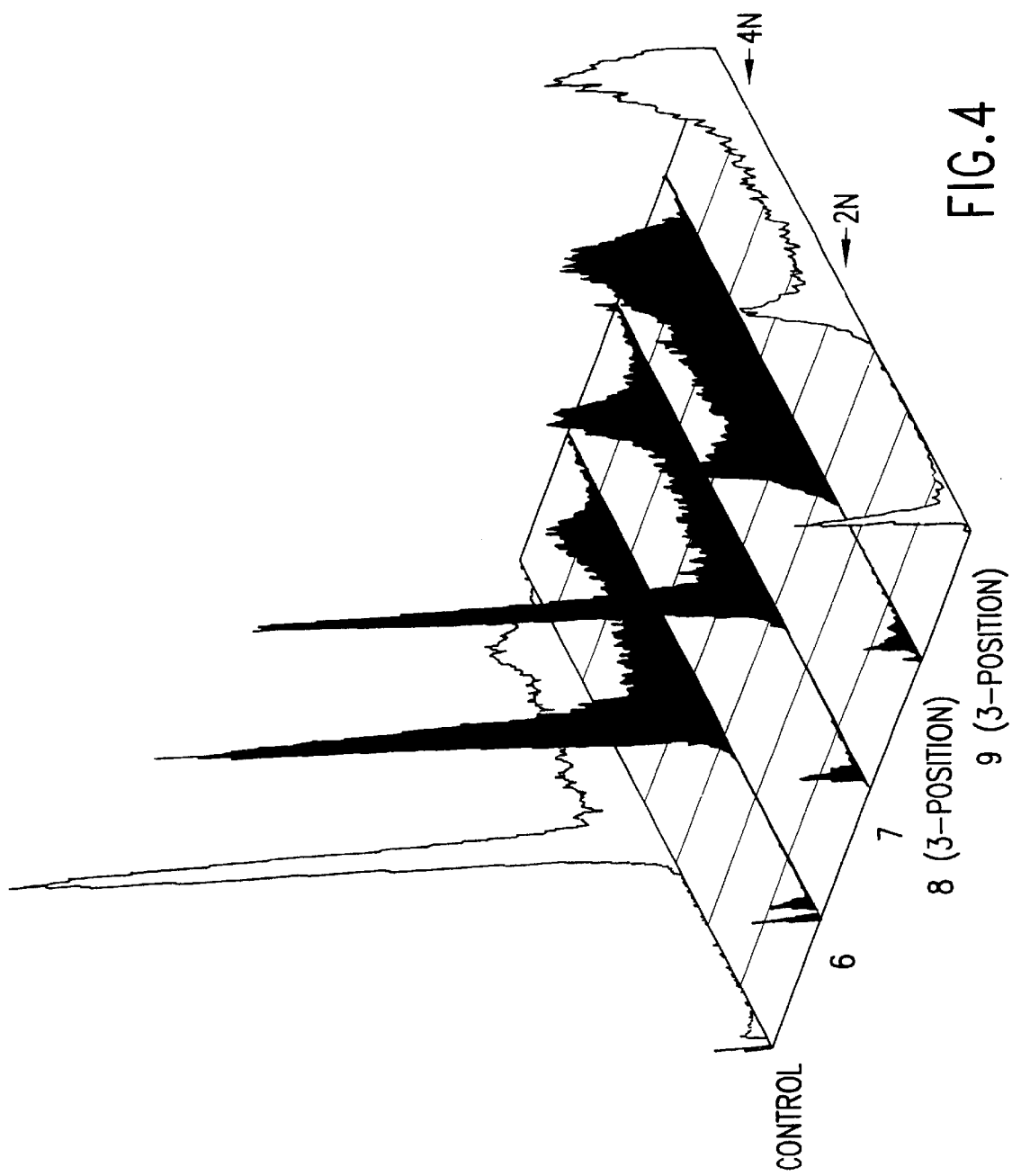
FIG. 4 is a 3-D graph of the accumulation of CEM leukemic cells at M-phase ascertained by cell cycle analysis with flow cytometry. After 8 hours of treatment, the four halogenated compounds (compounds 6–9 shown in FIG. 1) showed different degrees of shift from G0/G1(2N) to G2/M (4N) phase, ranging from undetectable change with the fluorine substituted compound (compound 6, 2.5 $\mu$g/ml) to the most significant transformation with the iodine substituted compound (compound 9, 0.005 $\mu$g/ml).

These results were confirmed by cell cycle analysis (DNA content) with flow cytometry after an 8 h treatment. The DNA profile of the fluorine containing compound 6 (2.5 μg/ml) was identical to that of the untreated control (see FIG. 4). The chlorine compound 7 induced a slight increase in the G2/M (4N) phase as compared to the control. The bromine compound 8 (0.025 μg/ml) and the iodine compound 9 (0.005 μg/ml) produced a major shift of the cell population from G0/G1(2N) to G2/M (4N), revealing a significant accumulation of cells in the M phase.

After 24 hours treatment with the same concentrations, the fluorine compound still exhibited virtually no interference with the cell cycle, the chlorine compound induced approximately 30% mitotic arrest, while both the bromine and iodine compounds gave>85% mitotic arrest (see Table 1). Compounds which contained the halogen in the 4-position and those which did not contain urea failed to induce mitotic arrest in the 0.01–5.0 μg/ml concentration range (see Table 1).

6. Apoptosis

Treatment with compounds 8 or 9 for 24 hours resulted in the disappearance of nuclear membrane and disorientation and loose scattering of metaphase chromosomes in the cytoplasm (FIG. 3, Panels B and C). Treatment for 24–48 hours represented a transition period, during which most cells exhibited shrinkage and compacting of chromosomes. Treatment prolonged to 48 h led to complete apoptosis characterized by condensation and segmentation of nuclei as well as the separation of apoptotic bodies from the affected cells (FIG. 3, Panel D).

Figure 5:
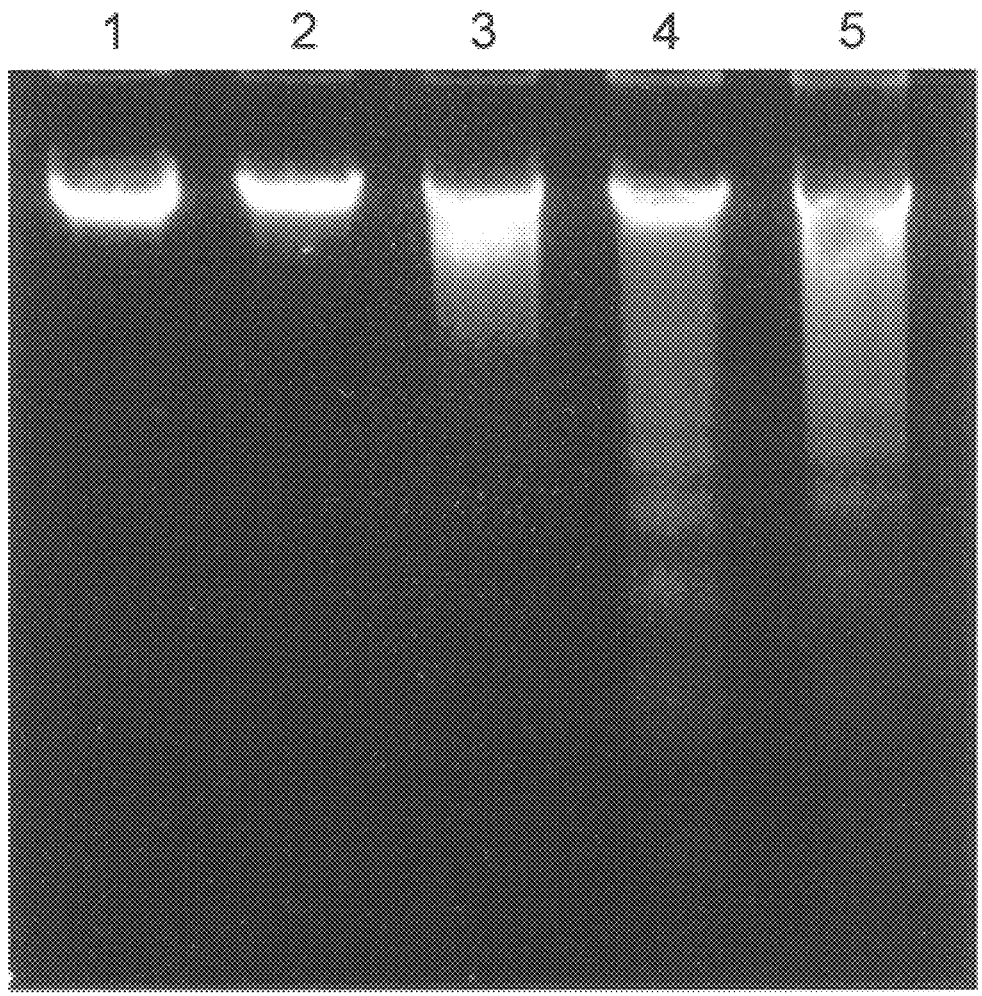
FIG. 5 is a photograph of a gel blot illustrating the significant cell death by apoptosis induced by the meta-substituted iodine and bromine acetoamido, benzoylurea derivatives of the present invention. CEM cells were treated separately with the individual compounds for 48 hours, followed by DNA fragmentation analysis using DNA gel electrophoresis. Lane 1=untreated CEM cells; lane 2 to 5=extracted DNA samples after treatment with compound 6 (5 $\mu$g/ml), compound 7 (0.7 $\mu$g/ml), compound 8 (0.025 $\mu$g/mi) and compound 9 (0.005 $\mu$g/ml), respectively.

DNA electrophoresis showed a 180–200 bp multiple-unit ladder pattern, representative of fragmented DNA in apoptotic cells (FIG. 5, lane 4 for compound 8 at 0.025 μg/ml and lane 5 for compound 9 at 0.005 μg/ml ). In contrast, the fluorine compound did not induce apoptosis even at a concentration of 5.0 μg/ml (FIG. 5, lane 2, control lane 1), while the chlorine compound (0.75 μg/ml) induced much less DNA fragmentation (FIG. 5, lane 3). The fact that apoptosis occurred subsequent to mitotic arrest, induced by compounds 8 or 9, is in agreement with similar observations with other antimicrotubule agents (references 8 & 9).

7. Inhibition of Microtubule Assembly

To establish whether the mitotic arrest activity of compounds 8 and 9 is due to their interference with any of the regulators or is due to a direct effect on the microtubule system, a pure, cell-free tubulin system was employed (see Materials and Methods described above). In the cell free system, the optical density increases as a function of time during the process of microtubule assembly and decreases during subsequent disassembly (after incubation at 0–4° C.).

Figure 6:
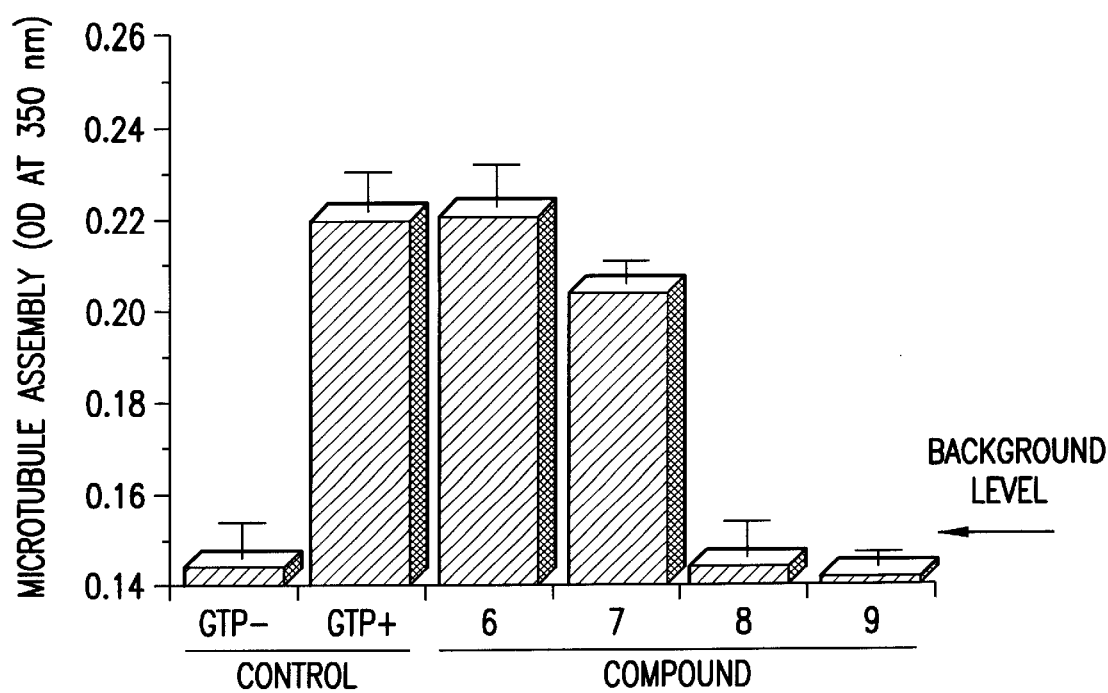
FIG. 6 is a bar graph illustrating the inhibition of microtubule assembly in a cell free system by the meta-substituted haloacetoamido, benzoylurea derivatives of the present invention: the bromine and iodine substituted compounds (compounds 8 and 9, 1 $\mu$g/ml) showed complete inhibition of the repolymerization of tubulin; the chlorine substituted compound (compound 7, 10 $\mu$g/ml) showed very weak inhibitory effect and the fluorine substituted compound (compound 6) showed no effect on the assembly of microtubules.

The fluorine and chlorine compounds 6 and 7 showed no effect on the process of microtubule assembly up to a concentration of 10 μg/ml (FIG. 6). In contrast, compounds 8 and 9 completely inhibited the normal microtubule assembly process at concentrations as low as 1 μg/ml, essentially the same as needed with vinblastine. At the same time, none of the compounds studied had any effect on microtubule disassembly at concentrations up to 10 μg/ml.

Example II

A. Materials and Methods

1. Candidate Compounds

3-Bromoacetylamino benzoylurea (3-BAABU; compound 8 in FIG. 1) and its analogs 3-chloroacetylamino benzoylurea (3-CAABU; compound 7 in FIG. 1), 3-bromoacetylamino benzoic acid ethyl ester (3-BAABE, compound 11), 4-bromoacetylamino benzoylurea (4-BAABU; compound 12) and 3-bromopropionylamino benzoylurea (3-BPABU; compound 13) were synthesized. Structures of these compounds, as shown in Table 2, were confirmed, by mass spectrometry and NMR. All compounds were dissolved in N,N-dimethyl acetamide, propylene glycol and Tween-80 in the proportions of 1:2:1 (v/v/v) and were further diluted in culture medium prior to use. Paclitaxel and vinblastine sulfate (Aldrich Chem. Co. Milwaukee., Mich.) were dissolved in dimethyl sulfoxide (DMSO) before use. Equal volumes-of solvents were used in experiments as controls.

2. Malignant & Non-Malignant Cells and Cell Lines

All cell lines, with the exception of human SP cells, a biphenotypic leukemic cell line (reference 10 & 11), were obtained from the American Tissue Culture Collection (Rockville, Md.) and were cultured under conditions recommended by the vendor. EL4 murine leukemia lymphoma (as suspension) and B16 mouse melanoma (as monolayer) cell lines were cultivated in RPMI-1640 medium supplemented with 10% fetal bovine serum (FBS), penicillin (250 $\mu$/ml) and streptomycin (250 $\mu$/ml); MOT, a non-tumor proliferative myocardial cell line from rat and NIH 3T3, a non-malignant and proliferative fibroblast cell line from mouse were both cultured as monolayers in Dulbecco's Modified Eagle's Medium with 10% heat inactivated calf serum. CEM, a human acute T-cell leukemic cell line, was cultured as a suspension in Iscove's Dulbecco's Medium with 10% heat inactivated fetal calf serum and antibiotics. PC-3 cells, a human prostate cancer line, was cultured as monolayers in RPMI-1640 with 10% FBS. SP cells were cultured in Minimum Eagle's Medium plus 10% FBS. Human peripheral blood lymphocytes (PBL) were isolated from whole blood of healthy individuals by Ficoll-Hypaque gradient method. Isolated PBL were maintained in RPMI-1640 in the presence of 10% homologous plasma at 37° C. All cells were incubated at 37° C. in 5% $CO_2$. Cells in exponential growth were used.

3. Cytotoxicity, $ID_{50}$ and $ID_{90}$ Determinations

Cells in suspension culture were seeded into 96-well microplates (Falcon, Oxnard, Calif.) at $10^5$ cell per well, followed, by treatment with 0–10 $\mu$g/ml of the candidate compounds for 48 hr at 37° C. with total volume of 250 $\mu$l per well. Cell viability was assessed by trypan blue exclusion.

For the monolayer cultures, cells were placed in 96-well microplates at $5 \times 10^4$ cells per well (250 $\mu$l/well). In the presence or absence of candidate compounds at concentrations between 0–10 $\mu$g/ml and incubated for 48 hr at 37° C. The supernatants were removed gently and the cells left in the wells were digested with EDTA-Trypsin in order to obtain homogeneous single cell suspensions for staining and counting.

The $ID_{50}$ and $ID_{90}$ was determined in duplicate in every set of experiments, and each experiment was repeated 3 times under identical conditions. $ID_{50}$ and $ID_{90}$ were defined as drug concentrations that induced 50% or 90% cellular death in comparison with untreated controls and calculated by non-linear regression analysis.

4. Anti-Tumorigenic Activity after Pulse Exposure

CEM cells were pulse exposed to 3-BAABU, 0.025 $\mu$g/ml at 37° C. for 60 min. After incubation, cells were washed twice in PBS. Cell pellets were resuspended in drug-free medium and incubated for 48 hr at 37° C. Cell viability, morphology, mitotic spindles, cell cycle distribution and apoptosis were determined 24 hr and 48 hr post pulse exposure.

5. Morphology by Microscopy

Cell samples on slides were prepared by a Cytospin centrifuge (Shandon Southern Products Ltd, England) at 700 g for 5 min. The slides were air dried, fixed in methanol and stained with Giemsa (Harleco, N.J.) at room temperature for 15 min. Alterations of nuclei, membranes and morphological features were observed by light microscopy. Cells in mitotic phase were recognized by the appearance of their chromosomes dispersed in the cytoplasm, and by the disappearance of nuclear membrane. Apoptotic-cells were identified using previously defined criteria, i.e., shrinkage in cell size, chromatin condensation and fragmentation of the nucleus into discrete masses (references 2 & 3). Necrotic cells were differentiated from apoptotic cells by observing swollen cytoplasm and the disappearance of cell membrane prior to the destruction of the nucleus.

6. DNA Fragmentation by Electrophoresis

Soluble DNA from cells was extracted by the method reported previously (14). Briefly, after washing with PBS, cells were treated in 1 ml lysis buffer (0.01 M Tris.HCL pH 8.0, 0.01 M NaCl, 0.01M EDTA pH 8.0 and 5% sodium dodecyl sulfate) containing 1 $\mu$g/ml proteinase K for 1 hr at 50° C. The resulting products were extracted with phenol and chloroform:isoamylalcohol (24:1, v/v), and precipitated with ethanol followed by centrifugation at 7800 g (SorvallRC-5B Du Pont, Newtown, Conn.). The ethanol was removed and the dry pellet of nucleic acid was resuspended in 10 mM Tris-HCL/1 mM EDTA solution. DNA content was determined spectrophotometrically by measuring absorption at 260 nm ($A_{260}$). All samples, had $A_{260}/A_{280} \geq 2$. The DNA samples were then treated with RNase (Sigma, St. Louis, Mo.) at a final concentration of 0.1 $\mu$g/l for 20 min at 37° C. before gel loading . The DNA sample (4 $\mu$g) was analyzed in 1.5% horizontal agarose gel prepared with 1% ethidium bromide. Electrophoresis was performed at 75 volts for 2 hours and the DNA migration was visualized under UV light.

7. Immunofluorescent Detection of Mitotic Spindles

CEM cells incubated in the absence or presence of 3-BAABU were collected and centrifuged in a Cytospin at 700 g for 5 min. The slides were air dried and fixed with methanol for 20 min at –20° C. The slides were incubated in PBS containing. 1% BSA at 37° C. for 30 min. After washing with PBS for 3 min, cells on the slides were covered with 30 $\mu$l anti-human $\beta$-tubulin monoclonal antibody (4 $\mu$g/ml) (Accurate Antibody, Westbury, N.Y.) and placed in a humid chamber at room temperature for 60 min. The slides were washed three times for 3 min each in PBS followed by staining with 10 $\mu$l FITC labeled goat anti-mouse antibody (Coulter, Hialeah, Fla.) in a humid chamber at room temperature for 60 min. After washing in, PBS, the immunofluorescent stained cells were visualized under a fluorescence microscope (Model MC 63, Zeiss, Germany).

8. Cell Cycle Analysis

Measurement of DNA content was accomplished as described by the manufacturer using a Cycle TEST kit purchased from Becton Dickinson (San Jose, Calif.). In all experiments, at least $10^4$ cell events were analyzed. Properties of the light-scattering (forward and sideward ) and DNA luminescence of individual cells were measured with FACScan flow cytometer using Cellfit software for gating analysis. (Becton Dickinson, San Jose, Calif.).

9. Inhibition Assay of Microtubule Assembly and Disassembly by Spectrophotometry Purified tubulin from calf brain was purchased from Sigma (St. Louis, Mo.). The effects of 3-BAABU (3-bromoacetoamido, benzoylurea) on the microtubule assembly-disassembly process were determined using the conditions recommended by the vendor. For assembly inhibition, 100 $\mu$l tubulin solution (500–600 $\mu$g protein/ml) was mixed gently with 400 $\mu$l reaction buffer containing 0.1

M MES, 1 mM EGTA, 0.5 mM $MgCl_2$, 0.1 mM EDTA and 2.5 M glycerol at 37° C. 3-BAABU, paclitaxel or vinblastine were then added to each sample cuvet at final concentrations of 3.3, 23 or 22 µM, respectively. After adding GTP to each sample to a final concentration of 1 mM, the microtubule assembly process was monitored by measuring the change of absorbance (OD) every 5 min at 350 nm on a spectrophotometer (Ultrospec III, Pharmacia LKB, Uppsala, Sweden). A completed assembly process was observed within 40 min at room temperature. For disassembly inhibition, 3-BAABU (3.3 µM), paclitaxel (23 µM) or vinblastine (22 µM) was added to a cuvet with repolymerized microtubules according to the method described above, and incubated in melting ice. Changes of absorbance (OD) were monitored at 350 nm for 30 min until the OD values in the controls returned to the starting level, i.e., completion of the assembly-disassembly cycle. Solvent solutions were used as control and had no effect in either the assembly or disassembly process.

B. Results and Discussion

1. Mitotic Arrest in Leukemic Cells by Candidate Compounds

Table 2 shows the structures of the candidate compounds studied, the $ID_{50}$ values and the activities of inducing mitotic block, apoptosis as well as necrosis. 3-BAABU showed powerful anti-leukemia activity, with $ID_{50}$ of 0.013 µM. When Br was substituted with Cl, forming 3-CAABU (3-chloroacetoamido, benzoylurea), $ID_{50}$ increased 40-fold. The replacement the urea group with an ethyl ester (3-BAABE) increased $ID_{50}$ 10-fold. When the bromoacetylamino group was moved from the meta- to the para-position (4-BAABU) the $ID_{50}$ level was similar to that of 3-BAABU. However, when the acetylamino chain was extended by one more methylene group forming 3-bromopropionylamino benzoylurca (3-BPABU) cytotoxic activity was eliminated.

Morphologically, treatment with 3-BAABU induced mitotic arrest of leukemic cells in various stages of early and middle M-phase (prometaphase/metaphase/anaphase). The cells possessed an intact plasma membranes but did not have nuclear membranes. Instead of interphase nucleus, most cells contained disorganized chromosomes in a loosely separated and dispersed distribution. 3-CAABU also induced mitotic arrest but with less disorganization than that of 3-BAABU. 3-BAABE caused apoptosis with condensation of nuclear chromatin. There was no apoptosis upon treatment with 4-BAABU, instead there was a loss of viability of the cells with swelling and rupture of the cell membrane which is characteristic of necrotic cell death.

2. Induction of Mitotic Blocking and Apoptosis by 3-BAABU

The details and time course of the effect of 3-BAABU on CEM cells was ascertained. Treatment with 3-BAABU (0.025 µg/ml, 37° C.) for up to 24 hr resulted in mitotic arrest of the CEM cells between prometaphase and anaphase. By 48 hr the cells left normal mitotic process and showed apoptosis with nuclear condensation, DNA fragmentation, cytoplasmic vacuolization and formation of apoptotic bodies. Study of the time course of 3-BAABU showed the earliest changes at 1 hr with enlargement and "rounding" of the nuclei, progressive arrest of the cells in M-phase, peaking of mitotic arrest at 24 hr, and exhibiting the onset of apoptosis at 48 hr. The DNA analysis on gel electrophoresis was in agreement with the changes observed in morphology and a clear multiple-units ladder pattern of apoptotic DNA was seen only at 48 hr after treatment.

3. Anti-Tumorigenic Activity of 3-BAABU

3-BAABU was highly effective and selective in inducing mitotic arrest and apoptotic cellular death in malignant cells. The $ID_{50}$ was 0.013 µg/ml for leukemic cells, 0.017 µg/ml for lymphoma, 0.05 µg/ml for prostate cancer cells and 0.07 µg/ml for melanoma. 3-BAABU failed to induce mitotic arrest or apoptotic cell death in normal human lymphocytes, proliferating fibroblast cells (3T3) or myocardial cells (MOT) (Table 3). $ID_{50}$ values for leukemic and lymphoma cell lines were 60 to 154 times lower than for non-malignant cells.

A one-hour pulse exposure of CEM cells to 3-BAABU resulted in irreversible mitotic arrest within the first 24 hr, followed by apoptotic cell death. The effects of one hour exposure and continuous incubation with CEM cells were similar (see Table 4).

The morphologic effect of 3-BAABU on a variety of human and murine tumor and non-malignant cell lines was ascertained. Treatment with 3-BAABU for 24 hr at 37° C. had no effect on normal human lymphocytes (2 µg/ml), rat myocardial cells (1.0 µg/ml), or murine fibroblast cells (1.0 µg/ml). However, 3-BAABU induced mitotic arrest in PC-3 human prostate cancer cells (0.1 µg/ml), murine melanoma cells (0.25 µg/ml) and SP human lymphoid leukemic cells (0.025 µg/ml).

4. Mitotic Arrest of Cem Cells at Spindle Assembly Checkpoint by 3-BAABU

Figure 7:
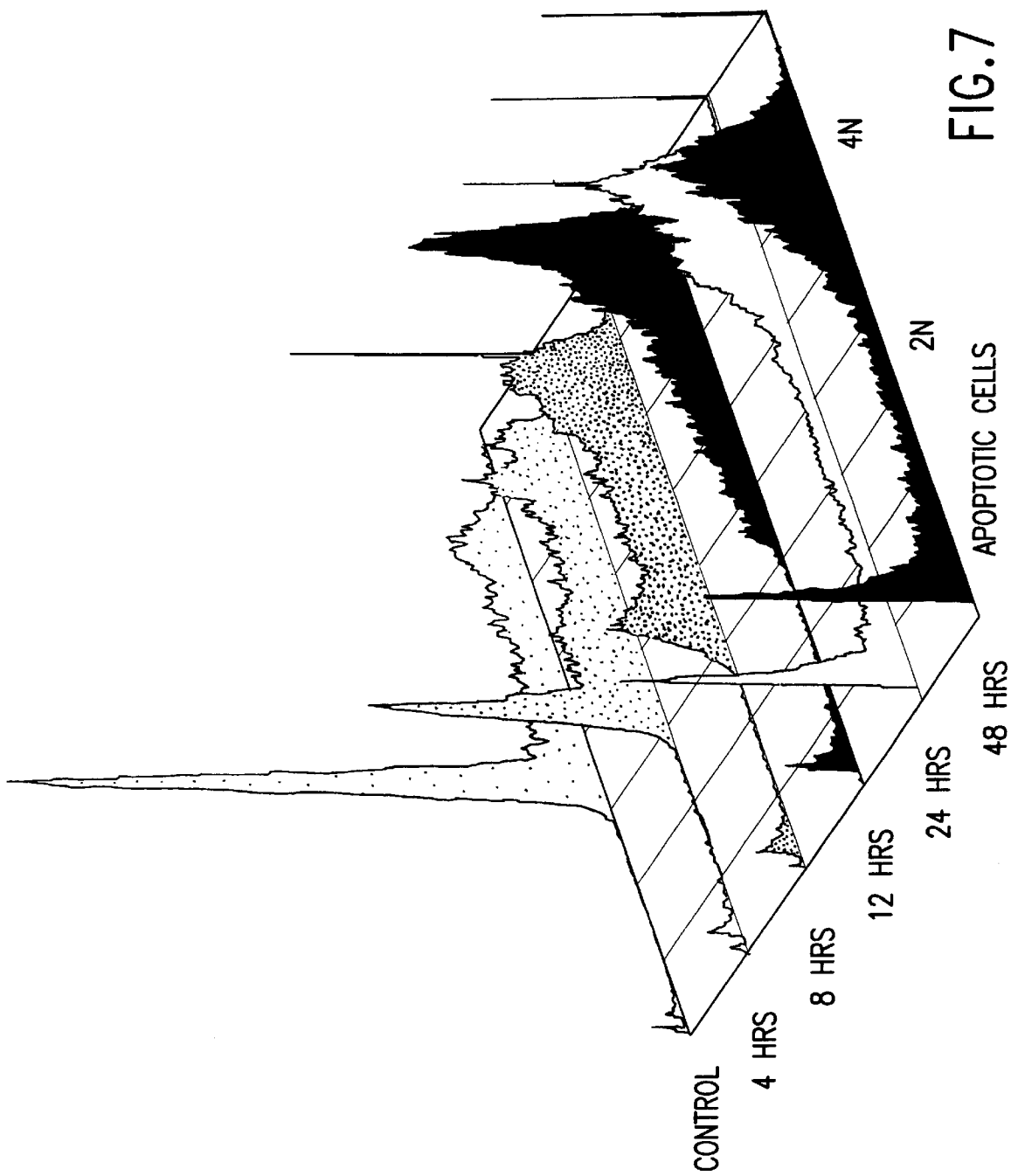
FIG. 7 is a 3-D graph of cell cycle analysis with flow cytometry illustrating the suspension of the cell cycle at G2/M phase in CEM cells treated with 0.025 $\mu$g/ml of 3-BAABU (i.e., compound 8) at 4, 8, 12, 24 and 48 hr after treatment, in comparison to untreated CEM cells. The majority of the 3-BAABU treated cells were accumulated at G2/M-phase 12 hr after treatment.
Figure 8A:
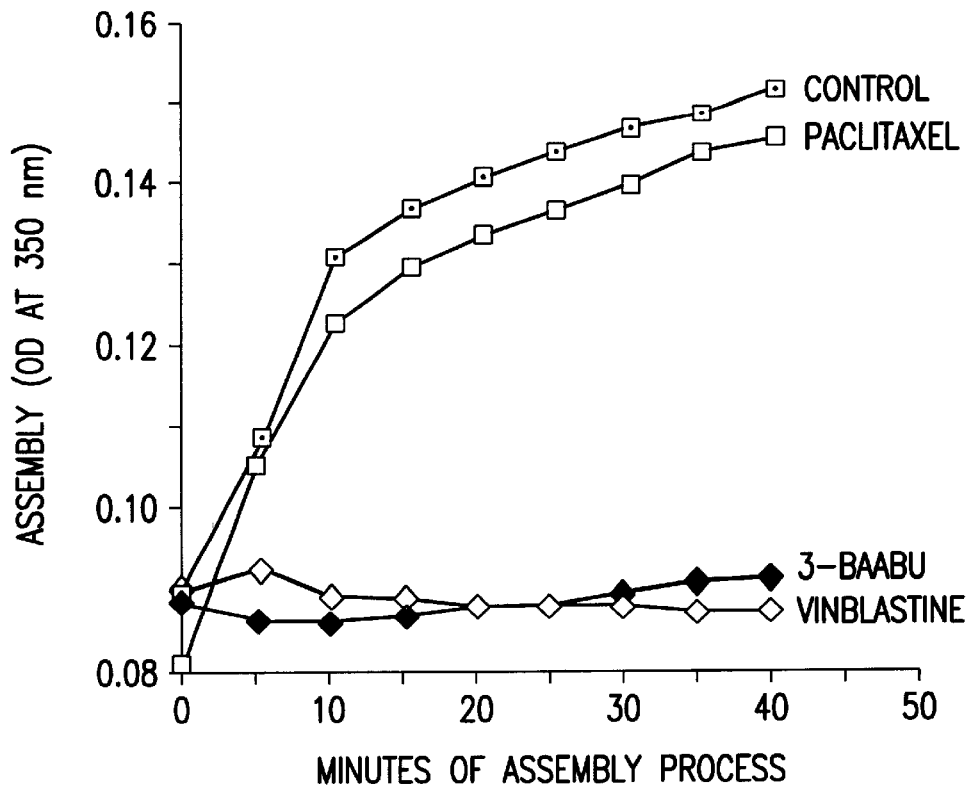
FIGS. 8A and B are plot graphs of the effect of 3-BAABU on heat-dependent polymerization-depolymerization cycle of microtubules in a cell free system.
Figure 8B:
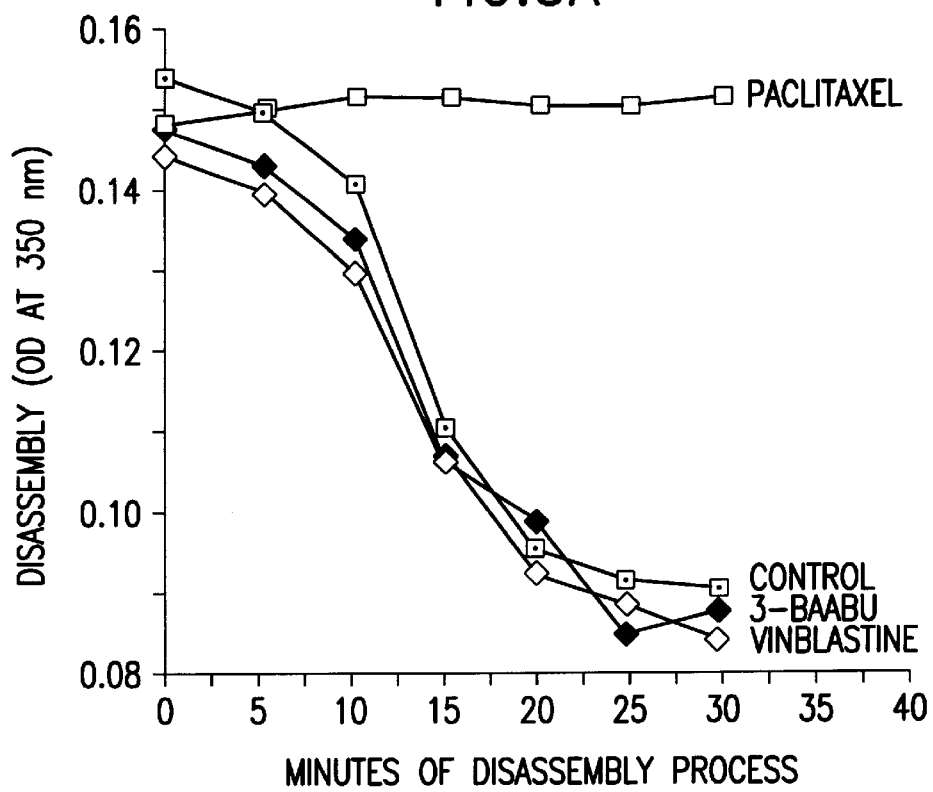
(FIG. 8B) for the disassembly process, assembled microtubules were incubated in ice in the absence, or presence of 3-BAABU or paclitaxel or vinblastine at concentrations mentioned above. The level of the microtubule assembly and disassembly was measured every 5 min by OD at 350 nm. Error bars are not shown to preserve clarity. SD (±) values (n=3) were in the 0.008–0.015 range.

CEM cells treated with 3-BAABU (0.025 µg/ml at 37° C.) for 0 to 48 hr were analyzed for their DNA distribution in cell cycle. As shown in FIG. 7 and Table 5, untreated CEM cells showed classical pattern of proliferating cells proportionally distributed in G0/G1 (50%), S (34%) and G2/M (13%) phases. 3-BAABU induced a major shift from G0G1 to G2/M phase. The detectable increase of G2/M phase cells was observed as early as 4 hr post-treatment and continuously increased with a reduction of the cells in G0G1 phase from 50% to 1%. Most cells were accumulated at G2/M phase by 12 hr, and the apoptotic cell proportion rose sharply thereafter. These changes were consistent with morphological observations and with analyses of DNA fragmentation.

5. Disruption of M-phase Specific Cytoskeletal Network by 3-BAABU

The distribution of β-tubulin and the formation of mitotic spindles in prometaphase/metaphase/anaphase in the cells treated with 3-BAABU was studied by immunofluorescent staining for β-tubulin. In the control group, about 12% of the CEM cells were in M-phase, clearly showing microtubule spindles characteristic of anaphase. Upon examination of several thousand mitotic cells arrested by 3-BAABU, none of them showed positive staining for mitotic spindles or astral microtubules. Instead, a homogeneous background staining of β-tubulin was noted in the cytoplasm.

6. Effect on Assembly-disassembly Cycles of Tubulin by 3-BAABU

The kinetics of microtubule assembly and disassembly of control, 3-BAABU, vinblastine and paclitaxel are shown in FIG. 6, Panels A and B. Untreated tubulins exhibited a temperature dependent assembly-disassembly cycle so long as Mg++ and GTP were present. 3-BAABU significantly inhibited the microtubule assembly process, but did not affect disassembly. Complete inhibition of microtubular polymerization was caused by 3-BAABU at a concentration as low as 1.0 µg/ml (3.3 µM), whereas microtubular depolymerization was not influenced even when the concentration of 3-BAABU was increased to 20 µg/ml (66 µM). Vinblastine showed a similar mechanism of action as 3-BAABU. In contrast, paclitaxel, which showed no activity on microtubular polymerization, exhibited significant inhibition of the process of microtubule depolymerization.

C. Concluding Remarks

As will be apparent to those skilled in the art, 3-BAABU (compound 6 in FIG. 1) caused significant accumulation of cells in mitosis, in which separated chromosomes appeared to be randomly distributed in the cytoplasm. The replacement of bromine with chlorine (3-CAABU; compound 7 in FIG. 1) or extending the side chain with one more methylene group to form bromopropionylamino benzoylurea (3-BPABU) largely or completely eliminated the mitotic blocking activity of the compound. The replacement of the urea group with an ethyl ester group (3-BAABE) removed the mitotic blocking activity and caused classical apoptotic cell death; while moving the bromoacetylamino group to the para-position on the benzene ring (4-BAABU) caused necrotic cell death. The comparisons of the bioactivity among the various analogs of the present invention indicate that the structure of 3-BAABU is preferred if anti-mitoitic activity is desired.

Kinetics of 3-BAABU activity in leukemic cells showed a 2-step process leading to cell death. In the first 24 hr, 3-BAABU interfered with key molecules essential for mitosis, and terminated the cell cycle in early or middle M-phase (prometaphase/metaphase/anaphase). In the second step (between 24 to 48 hr) cells accumulated in M-phase and then entered into apoptotic pathway, shown by the chromatin condensation and nuclear fragmentation characteristic of apoptosis. The process of apoptosis was further con finned, using gel electrophoresis, by the multiple unit DNA ladder pattern, which was in agreement with the time course of morphological observations.

The pulse exposure of leukemic cells to 3-BAABU yielded significant anti-tumorigenic effect in which both mitotic arrest and apoptotic cell death were subsequently observed, indicating a rapid uptake of 3-BAABU by target cells and irreversibility under the conditions studied. Since the cells that had only 1 hr exposure to 3-BAABU ended with a degree of mitotic blocking and apoptosis similar to those after 48 hr treatment, continuous presence of 3-BAABU is not required.

The data presented in Table 3 shows significant differences in cytotoxicity of 3-BAABU for malignant and non-malignant cells. The $ID_{50}$ values of the nonmalignant, proliferative cells were about 60–150 times higher than those for leukemia or lymphoma cells, indicating a highly selective toxicity of 3-BAABU. Since 3-BAABU inhibits repolymerization of tubulin, the preferential action against tumor cells is important.

Cell cycle analyses showed a major accumulation of G2/M (4 n) cells induced by 3-BAABU, concurrent with a significant reduction of cells in G0G1 (2 n) and S phase (2 n-4 n). Considering the cell cycle analyses together with morphological findings, it appears that the 4n peak at 12 hr contained a mixture of G2 and M phase cells, all of which then progressed into and arrested at prometaphase/metaphase/anaphase between 12–24 hr. After microscopic examination of over 50000 cells, no instance of telophase was seen.

Immunofluorescent assay with anti-β-tubulin monoclonal antibodies demonstrated a complete absence of mitotic spindles or mitotic astrals in the M-phase cells arrested by 3-BAABU, in contrast to the untreated cells which showed mitotic spindles in about 7–8% cells at various stages of mitosis. Since the cytoplasm showed homogenous background staining of βtubulin, it was assumed that 3-BAABU interfered with the assembly of microtubules from tubulins thus preventing the formation of mitotic spindles. The experiments of inhibition of repolymerization of tubulin in the cell-free system demonstrated that 3-BAABU abrogated the process of assembly of microtubule from tubulin, but did not interfere with the disassembly of microtubules.

Example III

The in vivo efficacy of 3-BAABU and 3-IAABU of the present invention was asssessed in a murine model, along with known anti-tubule agents, vinblastine and paclitaxel, as a comparative standard. Approximately $10^6$ P338 leukemia lymphoma cells/mouse were implanted intra-peritoneal (i.p.) into male C57 BL/6JX mice (Jackson Laboratories, NY). On days 2 and 8 post-implantation, drugs were administrated i.p. at the following concentration ranges: 3-BAABU from 16.6 to 116 μmole/kg, 3-IAABU from 14.4 to 101 μmole/kg, vinblastine from 2.2 to 20 μmole/kg and paclitaxel from 28 to 57 μmole/kg.

Figure 9:
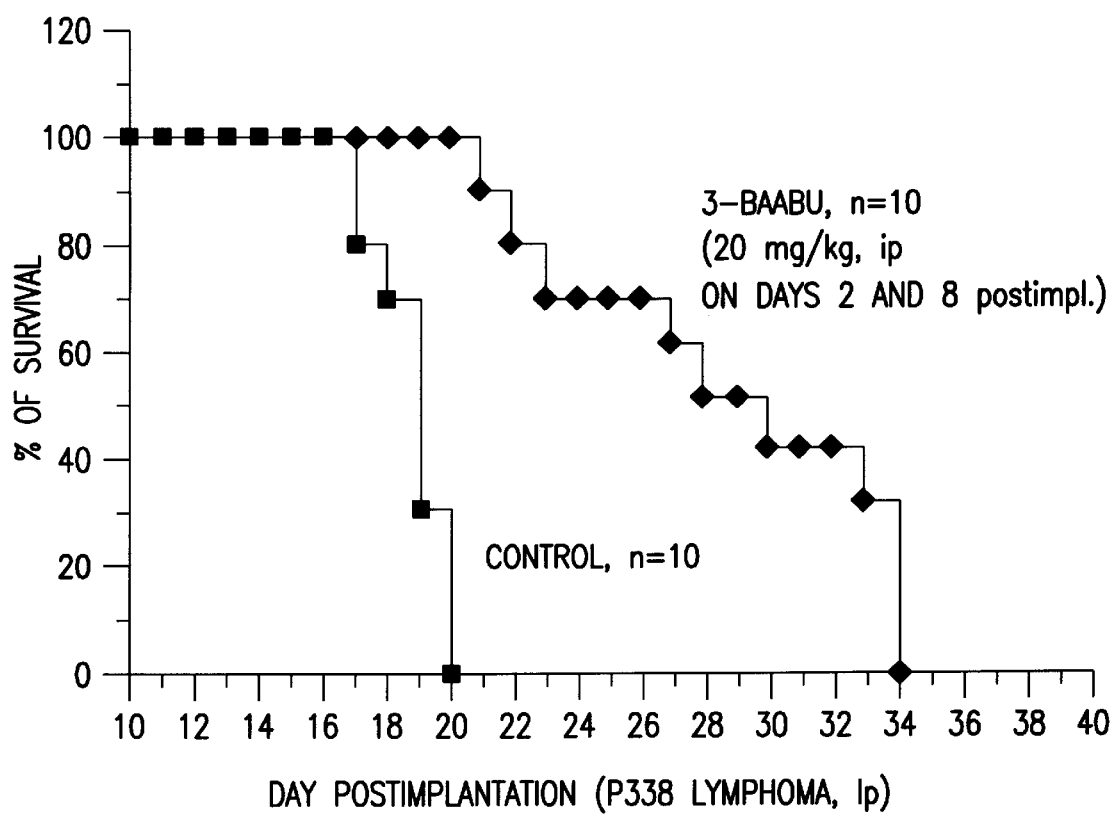
FIG. 9 is a plot graph of the survival rate of male C57 BL/6JX mice implanted (i.p.) with P338 lymphoma, from 10 to 40 days after implantation. Two groups were used for the study: a control group of ten and a test group of ten that were treated with 20 mg/kg, (i.p.) of compound 8 at 2 and 8 days post-implantation.

Both control and treated animals were examined for ascitic tumor burden daily for 35 days. All control mice exhibited ascites burden by day 12 and died 15 to 19 days post-implantation. The survival rates of mice implanted with L1210 Leukemia and P338 Lymphoma arc listed in Table 6, and with the survival rates for P338 Lymphoma being graphically depicted in FIG. 9. Therapeutic index was defined as the ratio of $LD_{50}$ (lethal dose) to $ED_{50}$ (effective dose).

Because the $LD_{50}$ of vinblastine was 9.2 μmole/kg and 45 μmole/kg for paclitaxel, the upper limit of the concentrations were selected as <20 μmole/kg and 58 μmole/kg for vinblastine and paclitaxel, respectively. This is in contrast to 3-BAABU and 3-IAABU for which $LD_{50}$ was about 90 μmole/kg, permitting the use of much higher concentrations, i.e., up to 116 μmole/kg. The following $ED_{50}$ were observed: 3-BAABU was 27 μmole/kg, 3-IAABU was 26 μmole/kg, vinblastine was 4.5 μmole/kg and paclitaxel was 37 μmole/kg. Accordingly, the therapeutic indices of compounds 8 and 9 were 3.4, in contrast to 2.0 for vinblastine and 1.2 for paclitaxel. Accordingly, the compounds of the present invention exhibited a higher selectivity than vinblastine and paclitaxel.

TABLES

TABLE 1

CYTOTOXICITY AND MITOTIC ARREST ACTIVITIES

| Compound[1] | Halogen | Position | $ID_{90}$[2] μg/ml | μM | Mitotic arrest, %[2] |
|---|---|---|---|---|---|
| Control | — | — | — | — | 8–10 |
| 6 | F | 3 | >2.5 | >10 | <10 |
| 7 | Cl | 3 | 0.6 | 2.3 | 20–30 |
| 8 | Br | 3 | 0.025 | 0.082 | >85 |
| 8 | Br | 4 | 0.15 | 0.497 | <10 |
| 9 | I | 3 | 0.005 | 0.014 | >85 |
| 9 | I | 4 | 0.04 | 0.112 | <10 |
| 10 (no urea) | Cl | 3 | 0.82 | 3.39 | <10 |
| 11 (no urea) | Br | 3 | 0.18 | 0.74 | <10 |

[1]For the identification of compounds 6–9 see FIG. 1 for reaction scheme; for compounds 10 and 11 see Materials and Methods of Example I.
[2]For description see Materials and Methods of Example I.

TABLE 2

STRUCTURE-ACTIVITY RELATIONSHIP OF
3-BROMOACETOAMIDO, BENZOYLUREA IN CEM LEUKEMIC CELLS

| Compound* | M.W** | $ID_{50}$ μg/ml | $ID_{50}$ μM | Mitotic block | Activities of inducing*** Apoptosis | Necrosis |
|---|---|---|---|---|---|---|
| 3-BAABE | 253 | 0.15 | 0.59 | − | ++++ | − |
| 3-BAABU | 300 | 0.013 | 0.04 | ++++ | ++++ | − |
| 4-BAABU | 300 | 0.07 | 0.23 | − | − | ++++ |
| 3-CAABU | 256 | 0.50 | 1.95 | + | ++ | − |
| 3-BPABU | 314 | NT | NT | − | − | − |

*For the abbreviations see Materials and Methods of Example II.
**Molecular weight.
***The level of activities are expressed by the % of affected cells. −: <10% + 10–25%,
++: 25–50%, +++; 50–75% and ++++; >75%.
NT Non-toxic to CEM cells

TABLE 3

PHASE SPECIFIC BLOCK OF CELL CYCLE
AT MITOSIS BY 3-BROMOACETOAMIDO, BENZOYLUREA IN
MALIGNANT CELLS*

| Cell | Type | Block of Mitosis | $ID_{50}$ (μg/ml) | $ID_{90}$ (μg/ml) |
|---|---|---|---|---|
| Tumor Cells: | | | | |
| SP | Human MDS** | + | 0.017 ± 0.003 | 0.71 ± 0.11 |
| CEM | Human T-cell Leukemia | + | 0.013 ± 0.002 | 0.02 ± 0.003 |
| PC-3 | Human Prostate Cancer | + | 0.05 ± 0.01 | 0.95 ± 0.17 |
| EL4 | Murine Lymphoma/Leukemia | + | 0.013 ± 0.003 | 0.02 ± 0.004 |
| B16 | Murine melanoma | + | 0.07 ± 0.014 | 0.76 ± 0.09 |
| Non-Tumor Cells: | | | | |
| PBL | Normal human PBL | − | >2.0 | ND |
| MOT | Rat myocardiac cells | − | >1.0 | ND |
| 3T3 | Murine fibroblast | − | >1.0 | ND |

*3-bromoacetoamido, benzoylurea was incubated with malignant or non-malignant cells at 37° C. for 48 hr. Mitotic arrest is defined as significant increase of mitotic cells (>50%) in comparison with controls.
**Myelodysplastic Syndrome.
+ Block of mitosis was observed;
− no mitotic blocking.
ND Not done.

TABLE 4

COMPARISON BETWEEN PULSE AND CONTINUOUS
EXPOSURE OF CEM TUMOR CELLS TO 3-BROMO-
ACETOAMIDO, BENZOYLUREA

| Activities | Exposure to 3-BAABU* Pulse Exposure (1 hr) | Continuous Exposure (24 hr) |
|---|---|---|
| $ID_{50}$ | 0.015 μg/ml | 0.013 μg/ml |
| Mitotic Arrest** | ++++ | ++++ |
| Antimicrotubule*** | ++++ | ++++ |
| Apoptosis**** | ++++ | ++++ |

*For pulse exposure, CEM cells were exposed to 3-bromoacetoamido, benzoylurea (3-BAABU) (0.025 μg/ml) for 60 min at 37° C., followed by washing twice in PBS. The cells were then cultured in 3-BAABU-free medium for 48 hr. For the continous exposure, CEM cells were incubated with 3-BAABU (0.025 μg/ml) for 48 hr. For the tests in this table, see Materials and Methods.
**Mitotic arrest was determined by cell cycle analyses.
***Antimicrotubule activity was tested by immunofluorescent staining.
****Apoptosis was examined by DNA electrophoresis.
++++: >75% cells were affected.

TABLE 5

BLOCKING OF CELL CYCLE AT M-PHASE CHECKPOINT BY
3-BROMOACETOAMIDO, BENZOYLUREA IN CEM LEUKEMIC
CELLS*

| Treatment | Hours of Treatment | G0/G1 (%) | S (%) | G2/M (%) | Apoptosis (%) |
|---|---|---|---|---|---|
| Untreated cells | | 49 | 35 | 14 | 2 |
| Solvent treated cells | 24 | 50 | 34 | 13 | 3 |
| 3-BAABU (0.025 μg/ml) | 1 | 48 | 29 | 21 | 2 |
| | 2 | 35 | 42 | 22 | 1 |
| | 4 | 28 | 39 | 29 | 4 |
| | 8 | 16 | 35 | 44 | 5 |
| | 12 | 4 | 29 | 60 | 7 |
| | 24 | 2 | 10 | 70 | 18 |
| | 48 | 1 | 5 | 61 | 33 |

*CEM cells were incubated with or without 3-BAABU for a pre-determined period of time as indicated in the table. Cell cycle analysis was performed as described in the Material and Methods of Example I.

TABLE 6

ANTI-TUMORIGENIC ACTIVITY OF 3-BROMOACETOAMIDO, BENZOYLUREA IN EXPERIMENTAL MICE MODELS

| Tumor (i.p.) | Group | n | Dose (ip) | schedule* | Survival Mean ± SD | IL % | p** |
|---|---|---|---|---|---|---|---|
| L1210 Leukemia | Control | 10 | — | on days 2 & 8 | 16.5 ± 1.4 | | |
| | 3-BAABU | 15 | 20 mg/kg | on days 2 & 8 | 23.7 ± 4.4 | 44 | 0.0001 |
| P338 Lymphoma | Control | 10 | — | on days 2 & 8 | 18.6 ± 1.1 | | |
| | 3-BAABU | 10 | 20 mg/kg | on days 2 & 8 | 28.6 ± 5.2 | 54 | 0.00001 |
| | Paclitaxel | 10 | 30 mg/kg | on days 2 & 8 | 20.4 ± 3.2 | 10 | 0.1653 |
| | Control | 20 | — | on days 2 & 8 | 15.1 ± 2.3 | | |
| | Vinblastine | 20 | 2 mg/kg | on days 2 & 8 | 18.2 ± 6.3 | 21 | 0.04 |

*days after tumor ip implantation
**unpaired t-test.

BIBLIOGRAPHY

The following references, which have been previously referred to throughout the specification within parentheses ( ), are incorporated herein by reference to the extent consistent with the present invention.

1. Alberts, B., Bray, D., Lewis, J., Raff, M., Roberts, K. & Watson, J. D. The mechanics of cell division. In: *Molecular Biology of The Cell*. Alberts, B., Bray, D., Lewis, J., Raff, M., Roberts, K. & Watson, J. D. (eds), p. 911. Garland: New York. (1994).

2. Roboz, J., Jiang, J. D., Holland, J. F. & Bekesi G. J. Selective tumor apoptosis by MF 13, L-prolyl-L-m-[bis(chloroetheyl)amino]-phenylalanyl-L-norvaline ethyl ester, a new sarcolysin containing tripeptide. *Cancer Research*, 57:4795 (1997).

3. Shi, Y., Glynn, J. M., Guilbert, L. J., Cotter, T. G., Bissonnette, R. P., & Green, D. R. Role for c-myc in apoptotic cell death in T-cell hybridoma. *Science*, 257:212 (1992).

4. Budesinsky, Z., Emr, A., Musil, V. Perina, Z. & Zikmund. Synthetic antidiabetics. I. Derivatives of urea, thiourea, and guanidine. *Ceskoslov. Farm.*, 8:129 (1959).

5. Weisz, I., Roboz, J. & Bekesi, J. G. Acidic coupling and aminolytic TFA cleavage approaches in a new synthesis of L-m-sarcolysin containing antitumor tripeptide ester. *Tetrahedron Letters*, 37:563 (1996). 6. Weisz, I. & Otvos, L. Acylierung von Alkoholen, Aminen und Amine-Saltzen mit Sauerenkloriden in Gegenwart von Amiden. *Arch. Pharm.* (Weinheim, Germany), 318:766 (1985).

7. Weisz, I., Dudas, J., Gribovszki, P., Grega, J., Havleka, F., Kerekes, F., Marasvolgyi, S., Pinter, Z. & Szilágyi, Gy. N-substituted carbamate esters and carboxamides. Patent HU 14225, *Chem. Abtsr.*, 88:152278 (1978).

8. Takano, Y., Okudaira, M. & Harmon, B. V. Apoptosis induced by microtubule disrupting drugs in cultured human lymphoma cells. Inhibitory effects of phorbol ester and zinc sulphate. *Pathol. Res. Pract.*, 189:197 (1993).

9. Milas, L., Hunter, R. H., Kurdoglu, B., Mason, K. A., Meyn, R., Stephens, L. C. & Peters L. J. Kinetics of mitotic arrest and apoptosis in murine mammary and ovarian tumor treated with taxol. *Cancer Chemother. Pharmacol*, 35:297 (1995).

10. Banerjee, R., Bekesi, J. G., Tarcsafaivi, A., Sperber, K., Deak, G., Choi, H. S. H., Paronefto, F., Holland, J. F. and Acs, G. Productive non-lytic HIV-1 replication in a newly established human leukemic cell line. *Proc. Natl. Acad. Sci. U.S.A.*, 89:9996 (1992).

11. Bekesi, G. J., Banerjee, R., Jiang, J. D., Roboz, J. P., Tarcsafalvi, A., Holland, J. F. and Acs, G. Translocation of cytoplasmic antigen markers in a biphenotypic cell line derived from a patient with myclodysplastic syndrome. *Molecular and Cellular Differentiatioal*, 3(2):111 (1995).

12. Wyllie, A. H., Kerr, J. F. R. and Currie, A. R. Cell Death: *The Significance of Apoptosis*. *Inter. Rev. of Cytol.*, 68:251 (1980).

13. Kerr, J. F. R., Winterford, C. M., Harmon, B. V. Apoptosis: Its Significance in Cancer and Cancer Therapy. *Cancer*, 73(8):2013 (1994).

14. Shi, Y., Glynn, J. M., Guilbert, L. J., Cotter, T. G., Bissonnette, R. P., Green, D. R. Role for c-myc in ApoptoticCell Death in T-cell Hybridomas. *Science*, 257:212 (1992).

What is claimed is:

1. A meta-haloacetoamido, benzoic acid derivative, having the formula:

I

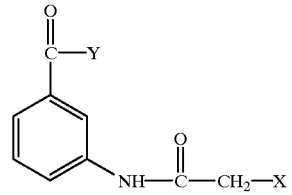

wherein X is a halogen selected from the group consisting of chlorine, bromine and iodine, and independently Y is a substituent selected from the group consisting of a urea group, an ethoxy group, —NH—CO—NH—R, wherein R is hydrogen, an alkyl group or an aryl group, and —N—$R_1$, wherein $R_1$ is an alkyl group or a heterocyclic group, or an acid addition salt thereof.

2. The haloacetoamido, benzoic acid derivative of claim 1, wherein said derivative is 3-iodoacetoamido, benzoylurea.

3. The haloacetoamido, benzoic acid derivative of claim 1, wherein said derivative is 3-bromoacetoamido, benzoylurea.

4. The haloacetoamido, benzoic acid derivative of claim 1, wherein said derivative is 3-chloroacetoamido, benzoylurea.

5. A formulation comprising a physiologically acceptable carrier and a haloacetamido, benzoic acid derivative of claim 1, or an acid addition salt thereof, in an amount effective to inhibit growth of malignant cells.

6. A para-haloacetoamido, benzoic acid derivative, having the formula:

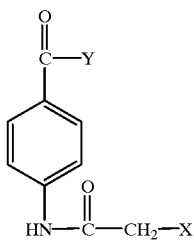

II wherein X is a halogen selected from the group consisting of chlorine, bromine and iodine, and independently Y is a substituent selected from the group consisting of a urea group, an ethoxy group, —NH—CO—NH—R, wherein R is hydrogen, an alkyl group or an aryl group, and —N—$R_1$, wherein $R_1$ is an alkyl group, a heterocyclic group or —N—$R_1$ is an amino acid ester, or an acid addition salt thereof.

7. The haloacetoamido, benzoic acid derivative of claim 6, wherein said derivative is 4-iodoacetoamido, benzoylurea.

8. The haloacetoamido, benzoic acid derivative of claim 6, wherein said derivative is 4-bromoacetoamido, benzoylurea.

9. The haloacetoamido, benzoic acid derivative of claim 6, wherein said derivative is 4-chloroacetoamido, benzoylurea.

10. A formulation comprising a physiologically acceptable carrier and a haloacetamido, benzoic acid derivative of claim 6, or an acid addition salt thereof, in an amount effective to inhibit growth of malignant cells.

* * * * *

UNITED STATES PATENT AND TRADEMARK OFFICE
CERTIFICATE OF CORRECTION

PATENT NO. : 6,294,695 B1
DATED : September 25, 2001
INVENTOR(S) : Bekesi et al.

It is certified that error appears in the above-identified patent and that said Letters Patent is hereby corrected as shown below:

Title page,
Item [56], References Cited, OTHER PUBLICATIONS,
Under Bekesi, "Myelodysplastic" should read -- Myclodysplastic --
Under Roboz, "Bis" should read -- bis --; "phenylkalanyl" should
read -- -phenylalanyl --; and "Cotnaining" should read -- Containing --
Under Weisz, (first occurrence) "L-rn-sarcolysm" should read -- L-m-sarcolysin --
Item [57], ABSTRACT,
Line 2, "inclosed." should read -- disclosed. --
Line 4, "benzoylurca," should read -- benzoylurea, --; and "3-bromoacctamido,"
should read -- 3-bromoacetamido, --
Line 5, "benzoylurca," should read -- benzoylurea, --

Column 2,
Line 30, "p-haloacctoamido," should read -- $p$-haloacetoamido, --
Line 54, "thereof'' should read -- thereof. --

Column 3,
Line 12, "as" should read -- an --

Column 4,
Line 11, "2.5 /$\mu$g/ml" should read -- 2.5 $\mu$g/ml --
Line 23, "$\mu$g/mi" should read -- $\mu$g/ml --

Column 5,
Line 30, "mioety" should read -- moiety --
Line 41, "ethyl-3-iodoacctoamido," should read -- ethyl-3-iodoacetoamido, --
Line 46, "describe" should read -- described --

Column 6,
Line 1, "($NC_6O_2H_{10}$)," should read -- ($NC_6O_2H_{10}$)), --
Line 10, "4-iodoacctoamido," should read -- 4-iodoacetoamido, --
Line 13, "ethyl-iodoacctoamido," should read -- ethyl-iodoacetoanudo, --
Line 34, "apara-substituted," should read -- a para-substituted, --

UNITED STATES PATENT AND TRADEMARK OFFICE
CERTIFICATE OF CORRECTION

PATENT NO. : 6,294,695 B1
DATED : September 25, 2001
INVENTOR(S) : Bekesi et al.

It is certified that error appears in the above-identified patent and that said Letters Patent is hereby corrected as shown below:

Column 7,
Line 23, "know" should read -- known --
Line 64, "Benzoylurca" should read -- Benzoylurea --

Column 8,
Line 7, "3" should read -- 3 --
Line 17, "crystalized" should read -- crystallized --
Line 34, "nine" should read -- ine --
Line 58, "Bromoacctoamido," should read -- Bromoacetoamido, --

Column 9,
Line 57, "HCL" should read -- HCl --
Line 62, "SorvallRC-5B" should read -- Sorvall RC-5B --
Line 64, "HCL" should read -- HCl --

Column 10,
Line 14, "(2-[N-moipholino]" should read -- (2-[N-moipholino] --
Line 26, "covets" should read -- cuvettes --
Line 65, "bromoaec-" should read -- bromoace- --

Column 11,
Line 2, "MHZ" should read -- MHz --
Line 10, "10,3013," should read -- 10.3013, --
Line 13, "$CH^2I$", should read -- $CH_2I$ --

Column 13,
Line 7, "volumes-of" should read -- volumes of --
Line 17, "$\mu$/ml" (both occurrences) should read -- $\mu$g/ml --

Column 14,
Line 6, "Apoptotic-cells" should read -- Apoptotic cells --
Line 16, "HCL" should read -- HCl --
Line 22, "SorvallRC-5B" should read -- Sorvall RC-5B --
Line 24, "HCL" should read -- HCl --

UNITED STATES PATENT AND TRADEMARK OFFICE
CERTIFICATE OF CORRECTION

PATENT NO. : 6,294,695 B1
DATED : September 25, 2001
INVENTOR(S) : Bekesi et al.

It is certified that error appears in the above-identified patent and that said Letters Patent is hereby corrected as shown below:

Column 15,
Line 3, "cuvet" should read -- cuvette --
Line 11, "cuvet" should read -- cuvette --
Line 28, "the" should read -- of the --
Line 34, "benzoylurca" should read -- benzoylurea --

Column 17,
Line 15, "ringe" should read -- ring --
Line 18, "anti-mitoitic" should read -- anti-mitotic --
Line 31, "con finned," should read -- confirmed, --

Column 18,
Line 4, "$\beta$tubulin" should read -- $\beta$-tubulin --
Line 13, "asssessed" should read -- assessed --
Line 16, "intra-peritoneal" should read -- intra-peritoneally --
Line 27, "arc" should read -- are --

Column 19,
Table 2, (fn), "+ 10-25%" should read -- +: 10-25% --
Table 3, "myocardiac" should read -- myocardial --
Table 3, (fn): "Myelodysplastic" should read -- Myclodysplastic --

Column 20,
Table 4, (fn), "continous" should read -- continuous --

Column 21,
Line 31, "(chloroetheyl)" should read -- (chloroethyl) --

UNITED STATES PATENT AND TRADEMARK OFFICE
CERTIFICATE OF CORRECTION

PATENT NO. : 6,294,695 B1
DATED : September 25, 2001
INVENTOR(S) : Bekesi et al.

It is certified that error appears in the above-identified patent and that said Letters Patent is hereby corrected as shown below:

Column 22,
Line 22, "*Differentiatioal,*" should read -- *Differentiation,* --
Line 32, "toticCell" should read -- totic Cell --
Line 35, "meta-" should read -- *meta-* --
Line 65, "haloacetamido" should read -- haloacetoamido --

Column 23,
Line 1, "para-" should read -- *para-* --

Column 24,
Line 15, "haloacetamido" should read -- haloacetoamido --

Signed and Sealed this

Twenty-first Day of January, 2003

JAMES E. ROGAN
*Director of the United States Patent and Trademark Office*